(12) United States Patent
Wang et al.

(10) Patent No.: US 11,378,509 B2
(45) Date of Patent: Jul. 5, 2022

(54) EVALUATION METHOD FOR HYDROGEN-BEARING COMPONENTS, POROSITY AND PORE SIZE DISTRIBUTION OF ORGANIC-RICH SHALE

(71) Applicant: China University of Petroleum(East China), Shandong (CN)

(72) Inventors: Min Wang, Shandong (CN); Jinbu Li, Shandong (CN); Zhiqiang Guo, Shandong (CN); Chuanming Li, Shandong (CN); Shuangfang Lu, Shandong (CN)

(73) Assignee: CHINA UNIVERSITY OF PETROLEUM(EAST CHINA), Shandong (CN)

( * ) Notice: Subject to any disclaimer, the term of this patent is extended or adjusted under 35 U.S.C. 154(b) by 518 days.

(21) Appl. No.: 16/484,440

(22) PCT Filed: Dec. 4, 2018

(86) PCT No.: PCT/CN2018/119193
§ 371 (c)(1),
(2) Date: Aug. 7, 2019

(87) PCT Pub. No.: WO2019/184429
PCT Pub. Date: Oct. 3, 2019

(65) Prior Publication Data
US 2020/0173902 A1 Jun. 4, 2020

(51) Int. Cl.
*G01N 15/08* (2006.01)
*G01N 33/24* (2006.01)

(52) U.S. Cl.
CPC ............ *G01N 15/08* (2013.01); *G01N 33/24* (2013.01); *G01N 2015/0846* (2013.01)

(58) Field of Classification Search
CPC ........ G01N 15/00; G01N 15/08; G01N 33/24; G01N 2015/0846
See application file for complete search history.

(56) References Cited

U.S. PATENT DOCUMENTS 10,156,531 B2 * 12/2018 Kwak .................. G01R 33/448
10,197,489 B2 * 2/2019 McCarty .................. C09K 8/66
(Continued)

OTHER PUBLICATIONS

The application of Nuclear Magnetic Resonance T1-T2 maps in the research of sedimentary organic matter: A case study of early mature shale with type I kerogen. Journal of Petroleum Science and Engineering. Yu Ma et al.. May 2019 (Year: 2019).*
(Continued)

*Primary Examiner* — Nguyen Q. Ha

(57) ABSTRACT

An evaluation method for hydrogen-bearing components, porosity and pore size distribution of organic-rich shale is provided, relating to a technical field of oil and gas development. The evaluation method includes steps of: according to differences among NMR (nuclear magnetic resonance) $T_1$-$T_2$ maps of kerogen, oil-adsorbed kerogen, clay minerals of different water-containing conditions, shale, dry shale sample, oil-saturated shale sample and water-saturated shale sample, establishing a classification scheme for each hydrogen-bearing component and a quantitative characterization method for fluid components of the organic-rich shale; with a $T_2$ distribution of the organic-rich shale after being saturated with oil as a target and a $T_2$ distribution of the dry shale sample as a basement, subtracting the basement, and obtaining a $T_2$ distribution of oil in pores; and based on the $T_2$ distribution of oil in the pores, evaluating the porosity and the pore size distribution of the organic-rich shale. Compared with a conventional method, the present invention
(Continued)

shows relatively high innovativeness and credibility, which is beneficial to perfecting analysis of NMR in shale petrophysical measurement.

5 Claims, 13 Drawing Sheets

(56) References Cited

U.S. PATENT DOCUMENTS 10,359,379 B2 * 7/2019 Tinni .................. G01N 24/081
10,466,186 B2 * 11/2019 Kadayam Viswanathan ...............
G01N 33/24

OTHER PUBLICATIONS

Cao et al., 2D-NMR Applications in Unconventional Reservoirs, SPE Canadian Unconventional Resources Conference, 2012, SPE 161578, pp. 1-17.
Hugh Daigle et al., Combining Mercury Intrusion and Nuclear Magnetic Resonance Measurements Using Percolation Theory, Transport in Porous Media, 2016, vol. 111, issue 3, pp. 669-679.
Gregory Gannaway et al., NMR investigation of Pore Structure in Gas Shales, SPE International Student Paper Contest at the SPE Annual Technical Conference and Exhibition, 2014, SPE-173474-STU, pp. 1-12.
Gao et al., Study on Selection Method of Core Nuclear Magnetic Resonance Experiment Parameters for Shale Reservoir, Chinese Journal of Engineering Geophysics, 2016, vol. 13, No. 3, pp. 263-270.
Adnan Al Hinai et al., Comparisons of pore size distribution: A case from the Western Australian gas shale formations, Journal of Unconventional Oil and Gas resources, 2014, vol. 8, pp. 1-13.
Somayeh Karimi et al., Reservoir Rock Characterization Using Centrifuge and Nuclear Magnetic Resonance: A Laboratory Study of Middle Bakken Cores, SPE Annual Technical Conference and Exhibition, 2015, SPE-175069-MS, pp. 1-18.
Ravinath Kausik et al., Dynamics and state of lipid bilayer-internal water unraveled with solution state 1H dynamic nuclear polarization, Physical Chemistry Chemical Physics, 2011, vol. 13, pp. 7732-7746.
Jean-Pierre Korb et al., Dynamics and Wettability of Oil and Water in Oil Shales, The Journal of Physical Chemistry, 2014, vol. 118, pp. 23212-23218.
Li et al., Research on movable fluids in shale gas reservoirs with NMR technology, Special Oil and Gas Reservoirs, 2012, vol. 19, No. 1, pp. 107-109 and 123-124.

Mansoor R. Ali et al., Characterizing Light Versus Bound Hydrocarbon in a Shale Reservoir by Integrating New Two-Dimensional NMR and Advanced Spectroscopy Measurements, Unconventional Resources Technology Conference, 2016, URTeC: 2457043, pp. 1-16.
Benjamin Nicot et al., Estimating Saturations in Organic Shales Using 2D NMR, International Symposium of the Society of Core Analysts, 2015, SCA1025-024, pp. 1-12.
Ning et al., Quantitative evaluation of pore connectivity with nuclear magnetic resonance and high pressure mercury injection: A case study of the lower section of ES3 in Zhanhua sag, Journal of China University of Mining and Technology, 2017, vol. 46, No. 3, pp. 578-585.
Qian et al., Experiments on shale reservoirs plugs hydration, Petroleum Exploration and Development, 2017, vol. 44, No. 4, pp. 615-621.
Erik Rylander et al., NMR T2 Distributions in the Eagle Ford Shale: Reflections on Pore Size, Unconventional Resources Conference-USA, 2013, SPE 164554, pp. 1-15.
M. Saidian et al., An Experimental Study of the Matrix-fracture Interaction During Miscible Displacement in Fractured Porous Media: A Micromodel Study, Energy Sources Part A, 2014, vol. 36, pp. 259-266.
Junchang Sun, Experimental Study of Micro-structure and NMR Features of Volcanic Gas Reservoir, Master Degree Thesis, Chinese Academy of Sciences, 2010.
Tan et al., NMR petrophysical interpretation method of gas shale based on core NMR experiment, Journal of Petroleum Science and Engineering, 2015, vol. 136, pp. 100-111.
Wang et al., Core Experimental Study on Paramagnetic Ion Effects on NMR Relaxation Property and Its Applications, Weil Logging Technology, 2003, vol. 27, No. 4, pp. 270-273.
Kathryn E. Washburn et al., Simultaneous Gaussian and exponential inversion for improved analysis of shales by NMR relaxometry. Journal of Magnetic Resonance, 2015, vol. 250, pp. 7-16.
Xu et al., A precise measurement method for shale porosity with low-field nuclear magnetic resonance: A case study of the Carboniferous-Permian strata in the Linxing area, eastern Ordos Basin, China, Fuel, 2015, vol. 143, pp. 47-54.
Yao et ai., Petrophysical characterization of coals by low-field nuclear magnetic resonance (NMR), Fuel, 2010, vol. 89, pp. 1371-1380.
Zhang et al., Nuclear magnetic resonance cryoporometry as a tool to measure pore size distribution of shale rock, Chinese Science Bulletin, 2016, vol. 21, pp. 2387-2394.
Zhou et al., NMR research of movable fluid and T2 cutoff of marine shale in South China, Oil and Gas geology, 2016, vol. 37, No. 4, pp. 612-616.

* cited by examiner

EVALUATION METHOD FOR HYDROGEN-BEARING COMPONENTS, POROSITY AND PORE SIZE DISTRIBUTION OF ORGANIC-RICH SHALE

CROSS REFERENCE OF RELATED APPLICATION

This is a U.S. National Stage under 35 U.S.C 371 of the International Application PCT/CN2018/119193, filed Dec. 4, 2018, which claims priority under 35 U.S.C. 119(a-d) to CN 201810260408.0, filed Mar. 27, 2018.

BACKGROUND OF THE PRESENT INVENTION

Field of Invention

The present invention relates to a technical field of oil and gas development, and more particularly to an evaluation method for hydrogen-bearing components, porosity and pore size distribution of organic-rich shale.

Description of Related Arts

Currently, the common techniques in the industry are described as follows.

The shale oil and gas is a hydrocarbon which is generated but retained in the micro-nano pores of the shale strata. In recent years, because of the huge resource amount, the shale oil and gas has attracted more attentions. In the initial stage of shale oil exploration, the shale oil in the organic-rich shale strata (TOC>2%, TOC=Total Organic Carbon) is the primary research subject, which is economically recoverable. Compared with the conventional sandstone reservoir, the organic-rich shale represents the characteristics of complex hydrogen-bearing components (high clay mineral content and rich organic matters) and compactness (low porosity and low permeability), causing that the conventional NMR (nuclear magnetic resonance) evaluation method has limitations on the hydrogen-bearing component identification and the porosity and pore size distribution characterization of the organic-rich shales.

Conventionally, the identification for the NMR signals of the hydrogen-bearing components in the shale is mainly based on the signal shielding method and the two-dimensional NMR method (Kausik et al., 2011; Cao et al., 2012; Gannaway, 2014; Karimi et al., 2015; Washburn et al., 2015; Daigle et al., 2016; Korb et al., 2014; Mansoor et al., 2016; and Nicot et al., 2016). The signal shielding method is to immerse the shale into the manganese chloride solution ($MnCl_2$) or saturate the shale with deuteroxide ($D_2O$), so that only the signal of oil is detected through the NMR.

(1) The identification based on the signal shielding method and the two-dimensional NMR method mainly faces following problems. ① When the manganese chloride or deuteroxide cannot enter the small pores or isolated pores in the shales, the signal of water may not be shielded. ② The lacustrine shale is enriched in clay minerals, and $Mn^{2+}$ will undergo hydrolysis with some clay minerals, which damages the pore structure of the shales (Wang et al., 2003). ③ These two methods can only separate the signals of oil and water, but cannot distinguish the signal of kerogen. The two-dimensional NMR method is to measure another parameter (e.g., diffusion coefficient D, longitudinal relaxation time $T_1$ and magnetic field gradient G) as well as the transverse relaxation time ($T_2$), and then separate each component according to the differences among the nuclear magnetic responses of different components. For the conventional reservoirs, the $D-T_2$ method is commonest. However, due to the characteristics of low porosity and much paramagnetic of shale reservoirs, the $D-T_2$ method cannot achieve the relatively good effect (Kausik et al., 2011; and Washburn et al., 2015). Conventionally, for distinguishing the hydrogen-bearing components of the shale, the widely used method by scholars is the NMR $T_1-T_2$ map (Kausik et al., 2011; Washburn et al., 2015; and Korb et al., 2014). However, there is little research on distinguishing the adsorbed fluid components and free fluid components in the shale; meanwhile, the research subject thereof is the marine shale, and whether it is applicable to the clay-rich lacustrine shale in China is still worth discussing.

In evaluation of the porosity and pore size distribution of the shale, some scholars have made several attempts (Yao et al., 2010; Rylander et al., 2013; Hinai et al., 2014; Saidian 2014; Xu et al., 2014; Tan et al., 2015; Zhang et al., 2016; Gao et al., 2016; Zhou et al., 2016; and Ning et al., 2017). The current experimental process is to optimize the test parameters (main objects are echo time (TE) and waiting time (TW)) of the NMR experiment with utilizing the porosity test results by the helium method, then measure the $T_2$ distribution of the water-saturated shale, and evaluate the porosity and pore size distribution of the shale (Li et al., 2012; Sun et al., 2010; Zhou et al., 2016; and Gao et al., 2016).

(2) The method of optimizing the test parameters of the NMR experiment with utilizing the porosity test results by the helium method faces following problems. ① The clay mineral content of the organic-rich shale is relatively high; with the water saturation method, it easily generates the hydration and expansion phenomenon (Qian et al., 2017), which damages the original pore structural features of the shale and causes the distortion of the porosity and pore size distribution of the NMR test. ② The value of TE calibrated with the test results by the helium method is generally 0.2 ms (some scholars adopt a larger value). Under the above TE test condition, the porosity of the NMR test is equal to that of the helium method; but theoretically, the test results thereof lost the signals of fluids in some nanometer pores with the relatively short relaxation time, and include part of the solid matrix signals. ③ The content of the organic matters in the organic-rich shale is high; the NMR $T_2$ distribution obtained through directly testing the shale sample includes many signals of solid organic matters and mineral structural water, and these signals are not the fluid components in the pores, which cannot be directly used in calculation of the porosity and pore size distribution.

In conclusion, because of the complexity of the organic-rich shale reservoir and many problems of the conventional NMR technology existing in the hydrogen-bearing component identification and the porosity and pore size distribution evaluation of the shale, it is urgent to develop an NMR evaluation method for the hydrogen-bearing component identification, the porosity and the pore size distribution of the organic-rich shale.

From the above description, it can be known that the prior art has problems that: there exist deficiencies in the identification of the hydrogen-bearing components in the shale by the $MnCl_2$-immersed shale or $D_2O$-saturated shale, and the $T_2$-D technology; the organic-rich shale expands after being saturated with water, and the pore structure is distorted; there exist deficiencies in the fluid detection of the micro-nano pores with the relatively short relaxation time in the organic-rich shale; and, the influences of the solid organic matter (kerogen) and mineral structural water on the porosity and pore size distribution characterization of the organic-rich shale are ignored.

The difficulties and meanings in solving the above technical problems are described as follows.

Compared with the conventional sandstone reservoir, the organic-rich shale has a large number of micro-nano pores and includes a great number of nuclear magnetic relaxation signals of organic matters/mineral structural water, and moreover, the nuclear magnetic relaxation features of the fluid in the micro-nano pores are relatively similar to that of the organic matters/mineral structural water, which increases the difficulties of the NMR technology in detection of the fluid signals of the small pores and interpretation of the hydrogen signals, resulting in that the evaluation method for the hydrogen-bearing component identification, the porosity and the pore size distribution is not perfect enough. Therefore, it is urgent to develop an evaluation method applicable to the organic-rich shale.

The meanings of the evaluation method are described as follows. The establishment of the NMR identification scheme for the hydrogen-bearing components in the shale is beneficial to the intuitive understanding of the relaxation features of each hydrogen-bearing component in the shale, especially the distribution features and contents of oil and water. For the organic-rich shale, under the condition of considering the NMR signals of kerogen and mineral structural water, with the fluid in the pores as the research subject, the above NMR technology has important significance on the physical characterization and microcosmic reservoir evaluation of the organic-rich shale. Meanwhile, the establishment of the NMR identification scheme for the hydrogen-bearing components in the shale provides the important technical supports for the oil and water occurrence form and mechanism research.

SUMMARY OF THE PRESENT INVENTION

A first object of the present invention is to provide an evaluation method for hydrogen-bearing components, porosity and pore size distribution of organic-rich shale, so as to solve problems in prior art.

The evaluation method for the hydrogen-bearing components, the porosity and the pore size distribution of the organic-rich shale comprises steps of:

according to differences among NMR (nuclear magnetic resonance) $T_1$-$T_2$ maps of kerogen, oil-adsorbed kerogen, clay minerals of different water-containing conditions, shale, dry shale sample, oil-saturated shale sample and water-saturated shale sample, establishing a classification scheme for each hydrogen-bearing component and a quantitative characterization method for fluid components of the organic-rich shale, which is beneficial to intuitive understanding of relaxation features of each hydrogen-bearing component in the organic-rich shale and identification of oil and water; and because NMR signals of organic matters and clay mineral structural water exist in the organic-rich dry shale sample, with a $T_2$ distribution of the organic-rich shale after being saturated with oil as a target and a $T_2$ distribution of the dry shale sample as a basement, subtracting the basement, and obtaining a $T_2$ distribution of oil in pores; and based on the $T_2$ distribution of oil in the pores, evaluating the porosity and the pore size distribution of the organic-rich shale, which is beneficial to an accurate determination of a fluid content and a pore size distribution range in the shale.

Preferably, the evaluation method for the hydrogen-bearing components, the porosity and the pore size distribution of the organic-rich shale particularly comprises steps of:

through contrastive analysis of the NMR $T_1$-$T_2$ maps of kerogen, oil-adsorbed kerogen, clay minerals of different water-containing conditions, and organic-rich shales of different oil-containing/water-containing conditions, determining the relaxation features of each hydrogen-bearing component, and establishing the classification scheme for signals of each hydrogen-bearing component in the organic-rich shale;

processing the organic-rich shale with oil extracting and drying, and obtaining the dry shale sample; dividing the dry shale sample into two parts, wherein one part is processed with pressurization and oil saturation for an NMR experiment, and the other part is for experiments of porosity with a helium method, low-temperature nitrogen adsorption, high-pressure mercury injection, and scanning electron microscope; and with the $T_2$ distribution of the organic-rich shale after being saturated with oil as the target and the $T_2$ distribution of the dry shale sample as the basement, subtracting the basement, and obtaining the $T_2$ distribution of oil in the pores; based on the $T_2$ distribution of oil in the pores, combined with a relationship between an NMR signal intensity and a volume of oil, evaluating the porosity of the organic-rich shale; and, combined with the experiments of low-temperature nitrogen adsorption, high-pressure mercury injection, and scanning electron microscope, establishing an NMR characterization method for the pore size distribution of the organic-rich shale.

Preferably, the kerogen and the oil-adsorbed kerogen are prepared through steps of:

crushing the organic-rich shale sample to above 100 meshes; immersing in distilled water for 4 hours; successively processing with an acid treatment (successively with 6 mol/L hydrochloric acid, 6 mol/L hydrochloric acid and 40% hydrofluoric acid), an alkali treatment (with 0.5 mol/L sodium hydroxide), and a pyrite treatment (with 6 mol/L hydrochloric acid and arsenic-free zinc powder); thereafter adding dichloromethane, and stirring; after the dichloromethane is volatilized, obtaining the oil-adsorbed kerogen; processing the oil-adsorbed kerogen with chloroform extraction for 24 hours, and obtaining the kerogen.

Preferably, the clay minerals of different water-containing conditions are prepared through steps of:

Because a content of illite-montmorillonite mixed-layer mineral in the organic-rich shale is relatively high, with montmorillonite as an example, firstly saturating the montmorillonite with water (free water and adsorbed water); and then drying for 24 hours respectively at 121° C. and 315° C.; wherein: under a water saturation condition, free water-containing montmorillonite is obtained; after drying at 121° C. for 24 hours, adsorbed water-containing illite is obtained; and, after drying at 315° C. for 24 hours, illite merely containing structural water is obtained.

Preferably, the organic-rich shales of different oil-containing/water-containing conditions are prepared through steps of:

because residual oil in the organic-rich shale is relatively heavy, firstly processing an as-received shale sample with chloroform extraction for 24 hours; then extracting the shale sample after chloroform extraction with a ternary organic solution MAB (a ratio of methyl alcohol, acetone and benzene is 15:15:70) having a relatively strong polarity for 24 hours, so as to remove the residual oil in the pores of the shale as far as possible; after ternary extraction, processing the shale sample after extraction with a high-temperature drying experiment until reaching a constant weight, wherein a drying temperature is set to be 315° C. and kept for 24 hours, so as to remove residual free water in the pores of the shale and residual bound/adsorbed water at surfaces of the pores, thereby obtaining the dry shale sample; and preserving the dry shale sample in a dryer (at a room temperature).

According to the present invention, the dry shale sample after extraction and drying is placed into a vacuum pressurization saturation device; the dry shale sample is firstly vacuumized for 24 hours with a vacuum degree of $1\times10^4$ Pa; and, after finishing vacuumizing, the dry shale sample is processed with pressurization and oil saturation or water saturation, wherein a pressurization time is 36 hours.

Preferably, the quantitative characterization method for the fluid components in the organic-rich shale comprises steps of:

(1) calibrating an NMR signal intensity and a volume of free/bulk oil/water, particularly comprising steps of:

configuring standard samples of oil and water with different volumes of 0.2 ml, 0.4 ml, 0.6 ml, 0.8 ml and 1.0 ml, and respectively processing with an NMR $T_2$ distribution test; according to the volume and a corresponding NMR $T_2$ distribution area of the free/bulk oil/water, establishing calibration formulas between the NMR signal intensity and the volume of the free/bulk oil and water that:

$$V_O = k_1 \times A_O \quad (1);$$

$$V_w = k_2 \times A_w \quad (2);$$

wherein: in the formulas, $V_O$ is the volume of the free/bulk oil, and $V_w$ is the volume of the free/bulk water, both in unit of ml; $A_O$ is the NMR $T_2$ distribution area of the free/bulk oil, and $A_w$ is the NMR $T_2$ distribution area of the free/bulk water, both in unit of a.u.; $k_1$ is a conversion coefficient between the NMR signal intensity and the volume of the free/bulk oil; and $k_2$ is a conversion coefficient between the NMR signal intensity and the volume of the free/bulk water; and (2) calibrating an NMR signal intensity and mass of adsorbed oil, particularly comprising steps of:

processing different dry shale samples with adsorbed oil; fitting relationships between the mass ($m_a$-$m_0$) and the NMR signal intensity ($T_{2a}$-$T_{20}$) of the adsorbed oil, wherein: $m_a$ and $T_{2a}$ are respectively mass and NMR $T_2$ distribution signal intensity of the dry shale sample with the adsorbed oil; and, $m_0$ and $T_{20}$ are respectively mass and NMR $T_2$ distribution signal intensity of the dry shale sample; and obtaining a calibration formula between the NMR signal intensity and the mass of the adsorbed oil that:

$$m_{a0} = k_a \times A_{a0} \quad (3);$$

wherein: in the formula (3), $m_{ao}$ is the mass of the adsorbed oil, in unit of mg; $A_{a0}$ is an NMR $T_2$ distribution area of the adsorbed oil, in unit of a.u.; and $k_a$ is a conversion coefficient between the NMR signal intensity and the mass of the adsorbed oil.

Preferably, evaluation for the porosity of the organic-rich shale comprises steps of:

acquiring an NMR $T_2$ distribution of saturating oil and calculating the porosity, particularly comprising steps of:

processing the oil-saturated shale sample with an NMR $T_2$ distribution test, and obtaining an NMR $T_2$ decay curve (S(t, sat)) of the oil-saturated shale sample; subtracting an NMR $T_2$ decay curve (S(t, dry)) of the dry shale sample from the NMR $T_2$ decay curve (S(t, sat)) of the oil-saturated shale sample, and obtaining the $T_2$ decay curve ($\Delta$S(t, oil)) of the saturating oil that:

$$S(t, \text{dry}) = \sum_i A_i \exp\left(-\frac{t}{T_{2i}}\right); \quad (4)$$

$$S(t, \text{sat}) = \sum_j A_j \exp\left(-\frac{t}{T_{2j}}\right); \quad (5)$$

$$\Delta S(t, \text{oil}) = S(t, \text{sat}) - S(t, \text{dry}) \quad (6)$$

$$= \sum_k \Delta A_k \exp\left(-\frac{t}{T_{2k}}\right);$$

wherein: in the formulas (4)-(6), S(t, dry) is an echo amplitude of the dry shale sample; S(t, sat) is an echo amplitude of the oil-saturated shale sample; $\Delta$S(t, oil) is an echo amplitude of the saturating oil; $A_i$ is an amplitude of the dry shale sample when $T_2 = T_{2i}$; $A_j$ is an amplitude of the oil-saturated shale sample when $T_2 = T_{2j}$; $\Delta A_k$ is an amplitude of the saturating oil when $T_2 = T_{2k}$; t=n*TE, wherein n is number of echoes; i, j and k respectively represent orders of signal collection points, with a value of 1, 2, 3 . . . n.

Preferably, NMR pore size calibration of the organic-rich shale comprises steps of:

determining an NMR calibration coefficient C; according to the formula (1), converting signal intensities corresponding to all $T_2$ points in the NMR $T_2$ distribution of the saturating oil to pore volumes; and, with a specified calibration coefficient C, converting a $T_2$ relaxation time to a pore diameter through a formula of:

$$d = C \times T_2 \quad (7);$$

wherein: in the formula (7), d is the pore diameter, in unit of nm; $T_2$ is an NMR transverse relaxation time, in unit of ms; and C is the calibration coefficient;

with a horizontal axis of pore diameter and a vertical axis of dV/(dlogD), graphing a pore size distribution curve $R_{NMR}$ converted from the NMR $T_2$ distribution of the saturating oil; superimposing curves of $R_{LTNA-MICP}$ and $R_{NMR}$, and calculating an error value thereof through a formula of:

$$Q = \frac{1}{n} \sum_{i=1}^{n} \sqrt{(R_{LTNA-MICP-i} - R_{NMR-i})^2} \quad (8)$$

$$= \frac{1}{n} \sum_{i=1}^{n} \sqrt{(R_{LTNA-MICP-i} - C \times T_{2i})^2};$$

wherein: in the formula (8), Q is the error value; n is a number of data points in the $R_{LTNA-MICP}$ pore size distribution curve; $R_{LTNA-MICP}$ is an $i^{th}$ data point in the $R_{LTNA-MICP}$ pore size distribution curve; and $R_{NMR-i}$ is $R_{NMR}$ data corresponding to the $i^{th}$ data point in the $R_{LTNA-MICP}$ pore size distribution curve;

when similarity of the curves of $R_{LTNA-MICP}$ and $R_{NMR}$ is closest, namely the error value is smallest, recording a current value of the calibration coefficient C as a pore diameter calibration coefficient value of the NMR transverse relaxation time.

A second object of the present invention is to provide a computer program able to implement the evaluation method for the hydrogen-bearing components, the porosity and the pore size distribution of the organic-rich shale.

A third object of the present invention is to provide an information data processing terminal able to implement the evaluation method for the hydrogen-bearing components, the porosity and the pore size distribution of the organic-rich shale.

A fourth object of the present invention is to provide a computer-readable storage medium containing instructions, wherein: when the computer-readable storage medium runs on a computer, the computer is able to execute the evaluation method for the hydrogen-bearing components, the porosity and the pore size distribution of the organic-rich shale.

A fifth object of the present invention is to provide an evaluation system for the hydrogen-bearing components, the porosity and the pore size distribution of the organic-rich shale, comprising:

a construction module for the classification scheme of the hydrogen-bearing components and the quantitative characterization method of the fluid components of the organic-rich shale, for establishing the classification scheme of each hydrogen-bearing component and the quantitative characterization method of the fluid components of the organic-rich shale according to the differences among the NMR $T_1$-$T_2$ maps of kerogen, oil-adsorbed kerogen, clay minerals of different water-containing conditions, shale, dry shale sample, oil-saturated shale sample and water-saturated shale sample; and an evaluation module for the porosity and the pore size distribution of the organic-rich shale, wherein: because the NMR signals of organic matters and clay mineral structural water exist in the organic-rich dry shale sample, with the $T_2$ distribution of the organic-rich shale after being saturated with oil as the target and the $T_2$ distribution of the dry shale sample as the basement, the $T_2$ distribution of oil in the pores is obtained through subtracting the basement, and based on the $T_2$ distribution of oil in the pores, the evaluation module evaluates the porosity and the pore size distribution of the organic-rich shale.

A sixth object of the present invention is to provide an information data processing terminal equipped with the evaluation system for the hydrogen-bearing components, the porosity and the pore size distribution of the organic-rich shale.

In conclusion, the present invention has following advantages and positive effects.

The present invention adopts the organic-rich shale as the analysis subject, and provides the NMR evaluation method for the hydrogen-bearing components, the porosity and the pore size distribution of the organic-rich shale, which solves and perfects following problems. Firstly, the established identification method for each hydrogen-bearing component (kerogen, adsorbed oil, free oil, adsorbed water, free water and mineral structural water) in the organic-rich shale with utilizing the NMR $T_1$-$T_2$ map technology is able to cover the shortages in the identification of the hydrogen-bearing components in the shale by the $MnCl_2$-immersed shale or $D_2O$-saturated shale, and the $T_2$-D technology, so that the accuracy of organic matter signal intensity detection can reach above 83% (as shown in FIGS. 14-16). Secondly, with the oil saturation method, the problems that the organic-rich shale expands after being saturated with water and the pore structure is distorted are solved. Thirdly, with the relatively low TE (echo time), the problem of fluid detection of the micro-nano pores with the relatively short relaxation time in the organic-rich shale is solved. Fourthly, through processing the organic-rich dry shale sample (the shale after oil extracting and drying) with pressurization and oil saturation and adopting the relatively low TE (0.07 ms), with the $T_2$ distribution of the organic-rich shale after being saturated with oil as the target and the $T_2$ distribution of the dry shale sample as the basement, the $T_2$ distribution of oil in the pores is obtained through subtracting the basement; and based on the $T_2$ distribution of oil in the pores, the porosity and the pore size distribution are evaluated, which eliminates the influences of the solid organic matter (kerogen) and mineral structural water on the porosity and pore size distribution characterization of the organic-rich shale. Compared with the conventional research method, the porosity by the present invention is closer to the porosity value by the helium measurement method (as shown in FIG. 17), and the pore size distribution shows high consistency in the small pores (<10 nm) with the low-temperature nitrogen adsorption experimental results (as shown in FIG. 18).

DETAILED DESCRIPTION OF THE PREFERRED EMBODIMENT

Figure 1:
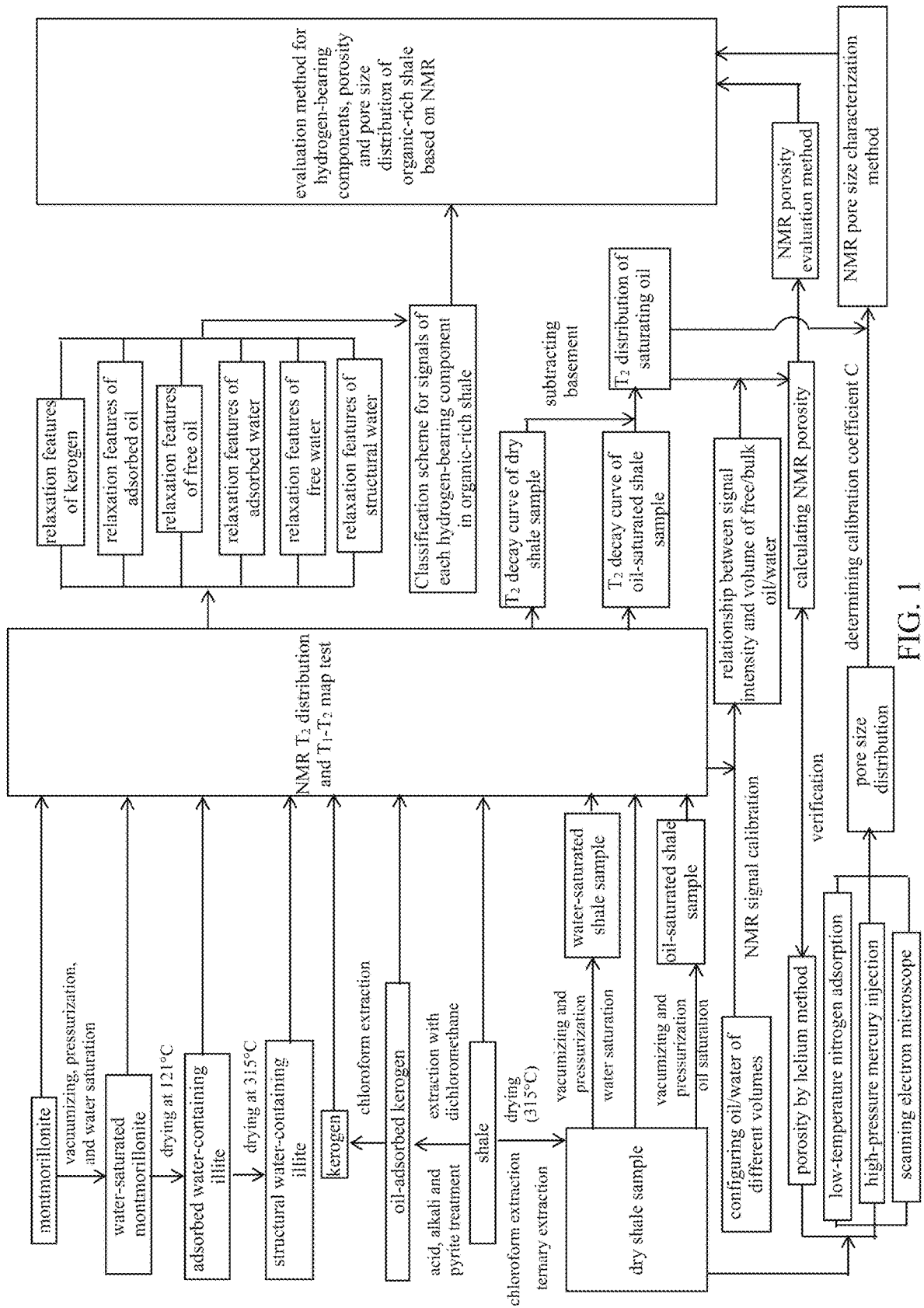
FIG. 1 is a flow chart of an evaluation method for hydrogen-bearing components, porosity and pore size distribution of organic-rich shale according to the present invention.

In order to make the objects, technical solutions and advantages of the present invention clearer and more understandable, the present invention is further described in detail with the preferred embodiment. It should be understood that: the preferred embodiment described herein is merely for explaining the present invention, not for limiting the present invention.

There exist deficiencies in the identification of the hydrogen-bearing components in the shale by the $MnCl_2$-immersed shale or $D_2O$-saturated shale, and the $T_2$-D technology; the organic-rich shale expands after being saturated with water, and the pore structure is distorted; there exist deficiencies in the fluid detection of the micro-nano pores with the relatively short relaxation time in the organic-rich shale; and, the influences of the solid organic matter (kerogen) and mineral structural water on the porosity and pore size distribution characterization of the organic-rich shale are ignored.

The present invention is further illustrated in detail as follows.

The present invention provides an evaluation method for hydrogen-bearing components, porosity and pore size distribution of organic-rich shale, comprising steps of:

with considering complexity of the hydrogen-bearing components in the organic-rich shale, according to differences among NMR (nuclear magnetic resonance) $T_1$-$T_2$ maps of kerogen, oil-adsorbed kerogen, clay minerals of different water-containing conditions, shale, dry shale sample, oil-saturated shale sample and water-saturated shale sample, establishing a classification scheme for each hydrogen-bearing component (kerogen, adsorbed oil, free oil, adsorbed water, free water, and mineral structural water) and a quantitative characterization method for fluid components of the organic-rich shale; and because NMR signals (enriched in organic matters and clay mineral structural water) which are relatively strong exist in the organic-rich dry shale sample, with a $T_2$ distribution of the organic-rich shale after being saturated with oil as a target and a $T_2$ distribution of the dry shale sample as a basement, subtracting the basement, and obtaining a $T_2$ distribution of oil in pores; and based on the $T_2$ distribution of oil in the pores, evaluating the porosity and the pore size distribution of the organic-rich shale.

The present invention is further illustrated in detail as follows.

The evaluation method for the hydrogen-bearing components, the porosity and the pore size distribution of the organic-rich shale based on the NMR can be divided into three parts, respectively the establishment of the NMR classification scheme for hydrogen-bearing components in the organic-rich shale, the NMR porosity evaluation of the organic-rich shale, and the NMR pore size distribution characterization of the organic-rich shale, particularly comprising steps of:

through contrastive analysis of the NMR $T_1$-$T_2$ maps of kerogen, oil-adsorbed kerogen, clay minerals of different water-containing conditions, and organic-rich shales of different oil-containing/water-containing conditions, determining relaxation features of each hydrogen-bearing component, and establishing the classification scheme for signals of each hydrogen-bearing component in the organic-rich shale;

processing the organic-rich shale with oil extracting and drying, and obtaining the dry shale sample; dividing the dry shale sample into two parts, wherein one part is processed with pressurization and oil saturation for an NMR experiment, and the other part is for experiments of porosity with a helium method, low-temperature nitrogen adsorption, high-pressure mercury injection, and scanning electron microscope; and with the $T_2$ distribution of the organic-rich shale after being saturated with oil as the target and the $T_2$ distribution of the dry shale sample as the basement, subtracting the basement, and obtaining the $T_2$ distribution of oil in the pores; based on the $T_2$ distribution of oil in the pores, combined with a relationship between an NMR signal intensity and a volume of oil, evaluating the porosity of the organic-rich shale; and, combined with the experiments of low-temperature nitrogen adsorption, high-pressure mercury injection, and scanning electron microscope, establishing an NMR characterization method for the pore size distribution of the organic-rich shale, as shown in FIG. 1.

The used NMR device in the present invention is a MicroMR23-060H-1 NMR analyzer of Shanghai Niumag Corporation, wherein: a resonance frequency is 21.36 MHz; a magnet intensity is 0.28 T; a coil diameter is 25.4 mm; and a magnet temperature is 32° C. The test of $T_2$ distribution adopts a CPMG sequence; and the test of $T_1$-$T_2$ map adopts an IR-CPMG sequence. Test parameters of the device are that: waiting time (TW) is 1000 ms; number of echoes (NECH) is 6000; echo time (TE) is 0.07 ms; P90 is 5.4 us; P180 is 10.6 us; number of scans (NS) is 64; and inversion time number (NTI) is 16.

The present invention is further illustrated in detail as follows.

Identification of Each Hydrogen-Bearing Component in Organic-Rich Shale

With taking lacustrine organic-rich shale as an example and adopting a separation method, according to test results of the NMR $T_1$-$T_2$ maps of kerogen, oil-adsorbed kerogen, clay minerals of different water-containing conditions, shale, dry shale sample after extraction and drying, water-saturated shale, and oil-saturated shale, establishing the classification scheme for the signals of each hydrogen-bearing component in the shale; extracting NMR signal intensities of organic matters, oil and water in the shale; and, based on the relationship between the NMR signal intensity and the volume of oil/water, estimating a oil/water saturation value of the shale. Detailed technical solutions are described as follows.

(1) Preparation of Kerogen and Oil-Adsorbed Kerogen

Crushing the organic-rich shale sample to above 100 meshes; immersing in distilled water for 4 hours; successively processing with an acid treatment (successively with 6 mol/L hydrochloric acid, 6 mol/L hydrochloric acid and 40% hydrofluoric acid), an alkali treatment (with 0.5 mol/L sodium hydroxide), and a pyrite treatment (with 6 mol/L hydrochloric acid and arsenic-free zinc powder); thereafter adding dichloromethane, and stirring; after the dichloromethane is volatilized, obtaining the oil-adsorbed kerogen; processing the oil-adsorbed kerogen with chloroform extraction for 24 hours, and obtaining the kerogen.

(2) Preparation of Clay Minerals of Different Water-Containing Conditions

Because a content of illite-montmorillonite mixed-layer mineral in the organic-rich shale is relatively high, with montmorillonite as an example, firstly saturating the montmorillonite with water (free water and adsorbed water); and then drying for 24 hours respectively at 121° C. and 315° C.; wherein: under a water saturation condition, free water-containing montmorillonite is obtained; after drying at 121° C. for 24 hours, adsorbed water-containing illite is obtained; and, after drying at 315° C. for 24 hours, illite merely containing structural water is obtained.

(3) Preparation of Shales of Different Oil-Containing/Water-Containing Conditions Because residual oil in the organic-rich shale is relatively heavy, firstly processing an as-received shale sample with chloroform extraction for 24 hours; then extracting the shale sample with a ternary organic solution MAB (a ratio of methyl alcohol, acetone and benzene is 15:15:70) having a relatively strong polarity for 24 hours, so as to remove the residual oil in the pores of the shale as far as possible; after ternary extraction, processing the shale sample with a high-temperature drying experiment until reaching a constant weight, wherein a drying temperature is set to be 315° C. and kept for 24 hours, so as to remove residual free water in the pores of the shale and residual bound/adsorbed water at surfaces of the pores, thereby obtaining the dry shale sample; and preserving the dry shale sample in a dryer (at a room temperature).

According to the present invention, the dry shale sample after extraction and drying is placed into a vacuum pressurization saturation device; the dry shale sample is firstly vacuumized for 24 hours with a vacuum degree of $1 \times 10^{-4}$ Pa; and, after finishing vacuumizing, processing the dry shale sample with pressurization and oil saturation or water saturation, wherein a pressurization saturation time is 36 hours.

(4) NMR Relaxation Features of Each Hydrogen-Bearing Component in Shale

The kerogen, oil-adsorbed kerogen, water-saturated montmorillonite, adsorbed water-containing illite, structural water-containing illite, shale, dry shale sample, oil-saturated shale and water-saturated shale, which are prepared through the above steps of (1)-(3), are processed with the NMR $T_1$-$T_2$ map test.

Figure 2:
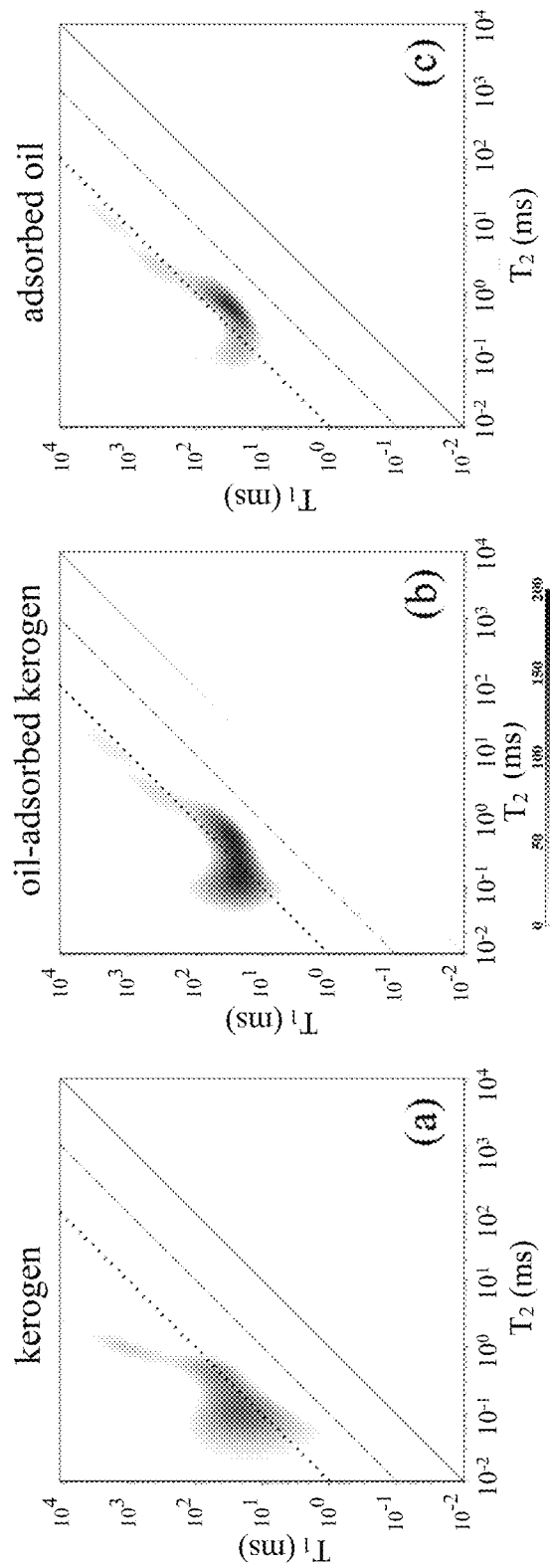
FIG. 2 shows NMR (nuclear magnetic resonance) $T_1$-$T_2$ maps of kerogen and oil-adsorbed kerogen according to the present invention.

The NMR $T_1$-$T_2$ maps of kerogen and oil-adsorbed kerogen are showed in FIG. 2. Under the mutual effect of homonuclear dipolar coupling, the transverse relaxation time of kerogen is relatively short, wherein: $T_2$ is distributed between 0.01-0.65 ms; a main peak is at about 0.1 ms; $T_1$ has a relatively wide distribution range and is mainly distributed between 0.65-100 ms; and a $T_1/T_2$ ratio is generally above 100. For the oil-adsorbed kerogen, $T_2$ is mainly distributed between 0.05-2 ms; a main peak is located at about 0.15 ms; $T_1$ is mainly distributed between 4.6-125 ms; and a $T_1/T_2$ ratio at the signal peak is about 155. Through subtracting the NMR $T_1$-$T_2$ map of the kerogen from the NMR $T_1$-$T_2$ map of the oil-adsorbed kerogen, the NMR $T_1$-$T_2$ map of the adsorbed oil is obtained (if a difference value is negative, set to be 0), wherein: for the adsorbed oil, $T_2$ is mainly distributed between 0.22-1 ms; a main peak is distributed at 0.65 ms; $T_1$ is mainly distributed between 10-125 ms; a $T_1/T_2$ ratio is between 25-200; and the $T_1/T_2$ ratio at the signal peak is about 50.

Figure 3:
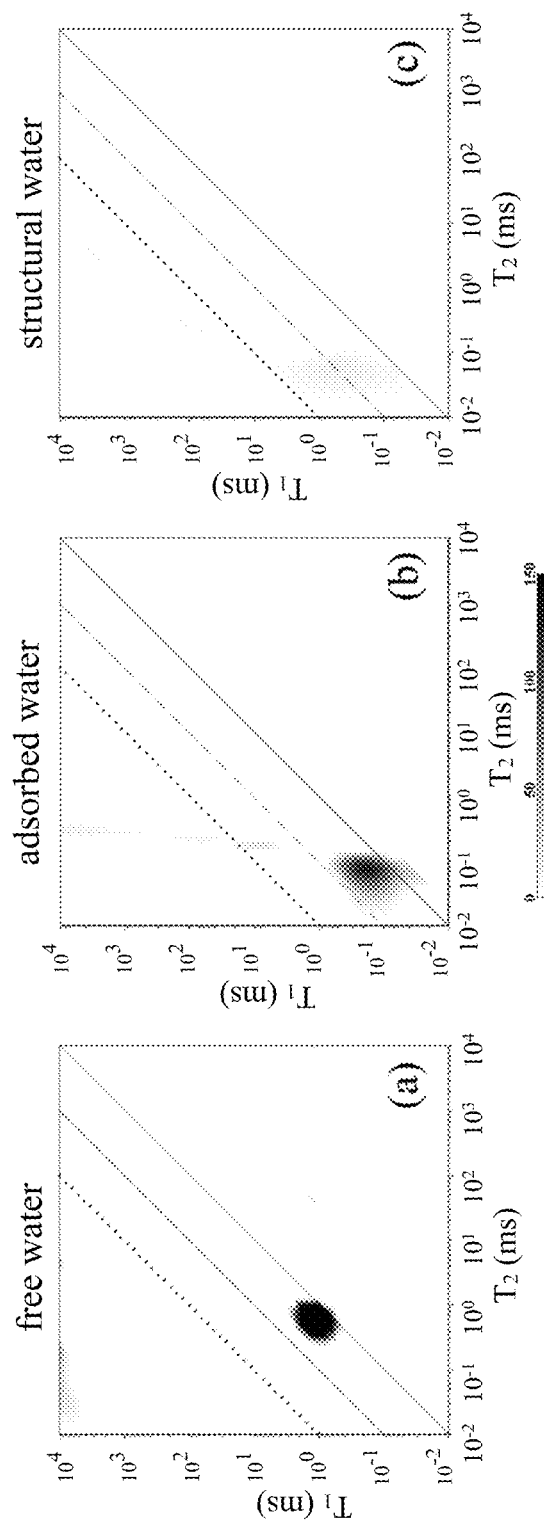
FIG. 3 shows features of an NMR $T_1$-$T_2$ map of free water in pores of montmorillonite after being saturated with water according to the present invention.

Features of the NMR $T_1$-$T_2$ map of free water in the pores of montmorillonite after being saturated with water are showed in FIG. 3, wherein: $T_2$ is mainly distributed between 0.22-1 ms; a main peak is located at 0.65 ms, a $T_1/T_2$ ratio is between 1-4.64; the $T_1/T_2$ ratio at the signal peak is about 1.94. After drying at 121° C., the interlayer water/free water is removed from montmorillonite, and montmorillonite is transformed into illite. For the adsorbed water-containing illite, $T_2$ is between 0.01-0.11 ms; a main peak is located at about 0.072 ms; $T_1$ is between 0.024-0.64 ms; a $T_1/T_2$ ratio is smaller than 10; and the $T_1/T_2$ ratio at the signal peak is about 3. After drying at 315° C., the adsorbed water at the surface of illite is removed, and the signal of structural water is detected by the NMR $T_1$-$T_2$ map test thereof. For the structural water, $T_2$ is between 0.01-0.11 ms; a main peak is located at about 0.058 ms; $T_1$ is between 0.058-26.83 ms; a $T_1/T_2$ ratio is smaller than 100; and the $T_1/T_2$ ratio at the signal peak is about 10.

Figure 4:
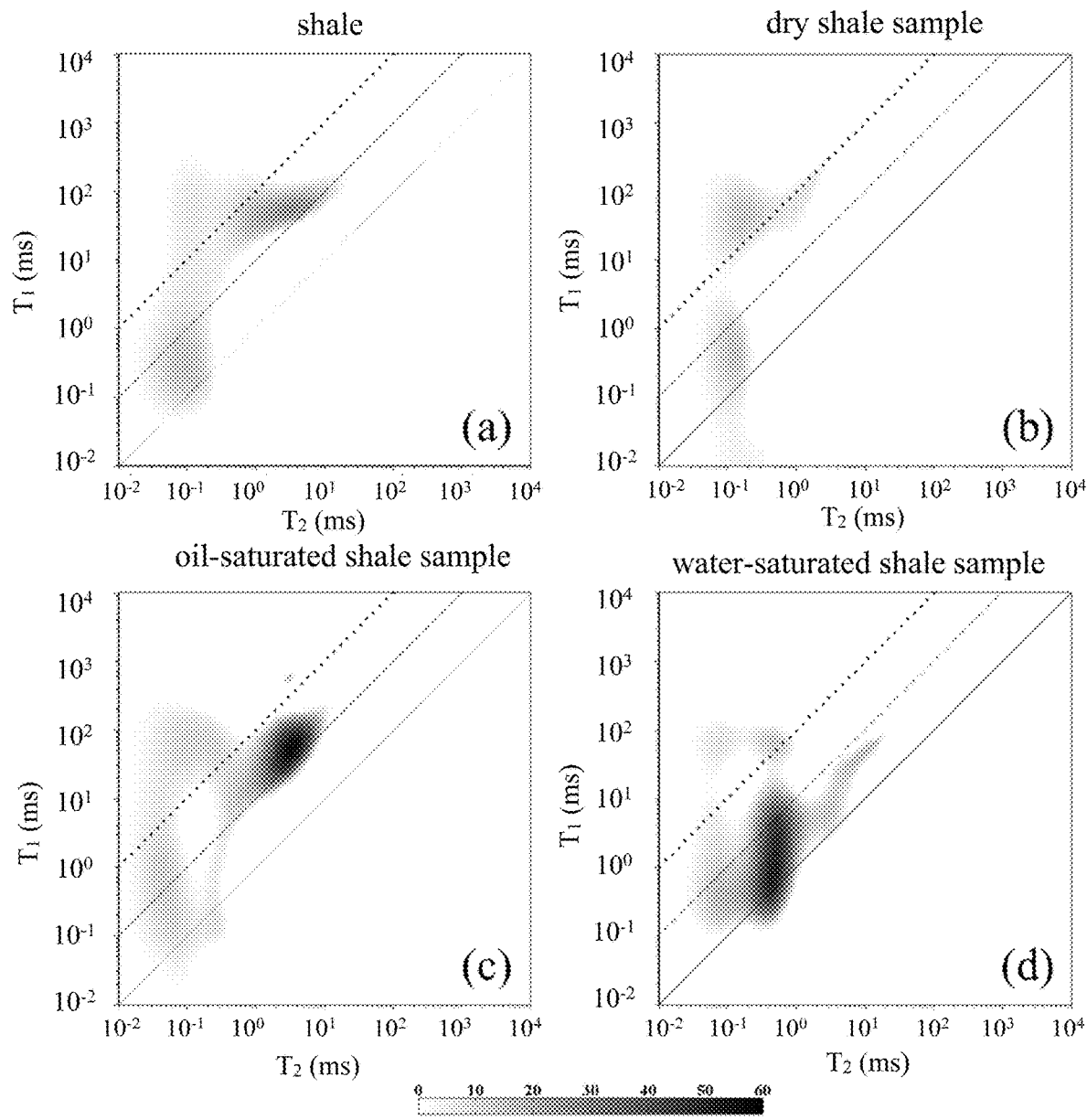
FIG. 4 shows NMR $T_1$-$T_2$ maps of shale, dry shale sample, oil-saturated shale sample and water-saturated shale sample according to the present invention.

The NMR $T_1$-$T_2$ maps of shale, dry shale sample, oil-saturated shale sample, and water-saturated shale sample are showed in FIG. 4. The NMR $T_1$-$T_2$ map of shale is mainly distributed in five areas that: kerogen signal ($T_2$<1 ms, $T_1/T_2$>100); adsorbed oil signal (0.22 ms<$T_2$<1 ms, 25<$T_1/T_2$<100); free oil signal ($T_2$>1 ms, 10<$T_1/T_2$<100); structural water signal ($T_2$<0.22 ms, $T_1/T_2$<100); and adsorbed water signal ($T_2$<0.22 ms, $T_1/T_2$<10). After processing the shale with chloroform extraction and drying at 315° C., compared with the NMR $T_1$-$T_2$ map of shale, the signal intensity of the free oil area ($T_2$>1 ms, 10<$T_1/T_2$<100) in the NMR $T_1$-$T_2$ map of dry shale sample is obviously decreased. However, the oil signal still exists in the free oil area of the dry shale sample, which may be part of the residual oil existing in the isolated pores and not completely removed during the processes of chloroform extraction and drying. After being saturated with oil, the signal intensity of the free oil area ($T_2$>1 ms, 10<$T_1/T_2$<100) is obviously increased. After being saturated with water, the signal intensities at the area of 0.22 ms<$T_2$<1 ms and $T_1/T_2$<10 and the area of 1 ms<$T_2$<10 ms and $T_1/T_2$<10 are obviously increased, indicating the free water. The signal intensity at the area of 0.22 ms<$T_2$<1 ms and $T_1/T_2$<10 is same as that of the water-saturated montmorillonite (as shown in FIG. 3), may indicating water in the clay mineral intercrystalline pores. For the area of 1 ms<$T_2$<10 ms and $T_1/T_2$<10, the $T_2$ relaxation time is relatively long, reflecting the intergranular pores with the relatively large size.

Classification Scheme for Signals of NMR $T_1$-$T_2$ Maps of Organic-Rich Shale

Figure 5:
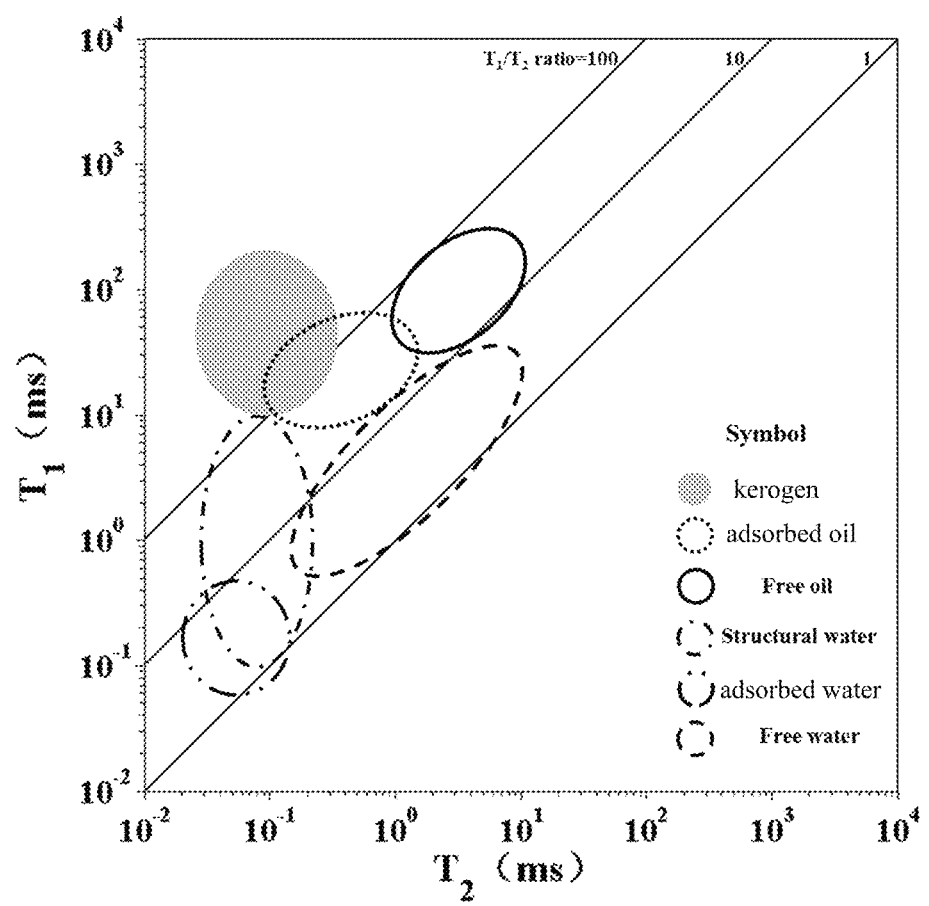
FIG. 5 is an NMR $T_1$-$T_2$ map of each hydrogen-bearing component in lacustrine shale according to the present invention.

According to the features of the NMR $T_1$-$T_2$ maps of kerogen, oil-adsorbed kerogen, clay minerals of different water-containing conditions, shale, dry shale sample after extraction and drying, oil-saturated shale sample, and water-saturated shale sample, the present invention provides the distribution range of each hydrogen-bearing component of the organic-rich shale in the NMR $T_1$-$T_2$ map, as shown in FIG. 5.

(5) Quantitative Characterization for Fluid Content in Organic-Rich Shale

1) Calibrating NMR Signal Intensity and Volume of Free/Bulk Oil/Water

Figure 6:
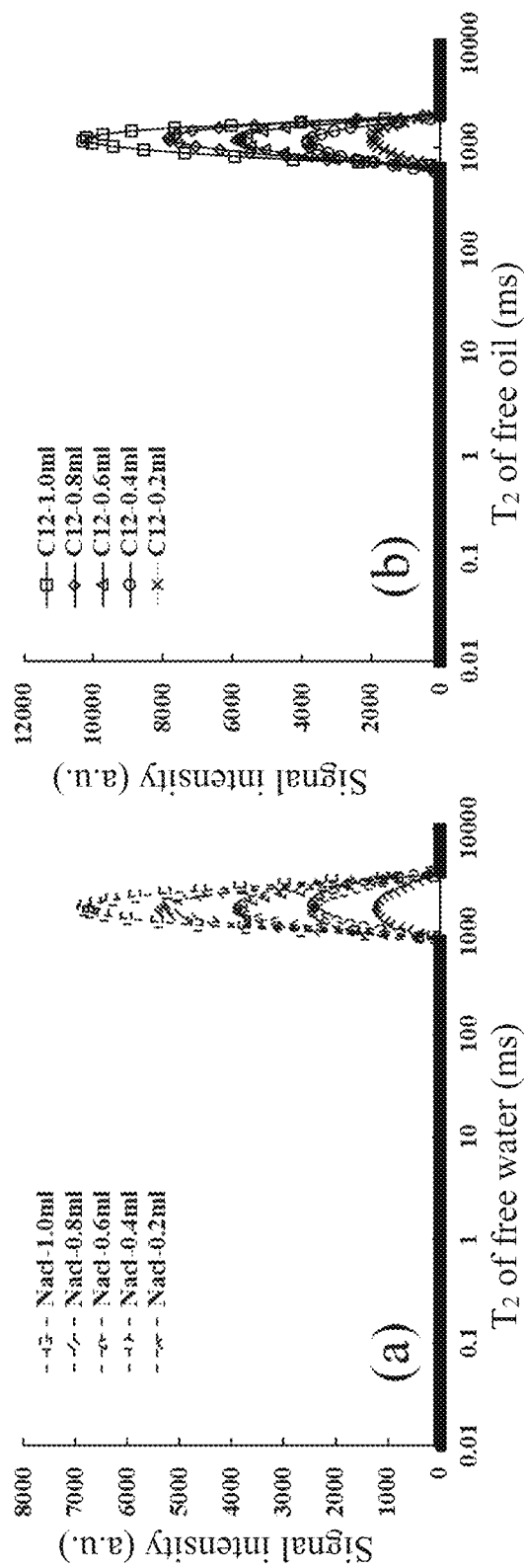
FIG. 6 is a distribution feature diagram of NMR $T_2$ distributions of free/bulk oil and free/bulk water with different volumes according to the present invention.

Configuring standard samples of oil and water with different volumes (0.2 ml, 0.4 ml, 0.6 ml, 0.8 ml and 1.0 ml), and respectively processing with an NMR $T_2$ distribution test, wherein the $T_2$ distributions of free/bulk oil and free/bulk water are showed in FIG. 6; according to a volume and a corresponding NMR $T_2$ distribution area of the free/bulk oil/water, establishing calibration formulas between the NMR signal intensity and the volume of the free/bulk oil and free/bulk water that:

$$V_O = k_1 \times A_O \tag{1};$$

$$V_w = k_2 \times A_w \tag{2};$$

wherein: in the formulas, $V_O$ is a volume of the free/bulk oil, and $V_w$ is a volume of the free/bulk water, both in unit of ml; $A_O$ is an NMR $T_2$ distribution area of the free/bulk oil, and $A_w$ is an NMR $T_2$ distribution area of the free/bulk water, both in unit of a.u.; $k_1$ is a conversion coefficient between the NMR signal intensity and the volume of the free/bulk oil; and $k_2$ is a conversion coefficient between the NMR signal intensity and the volume of the free/bulk water.

Figure 7:
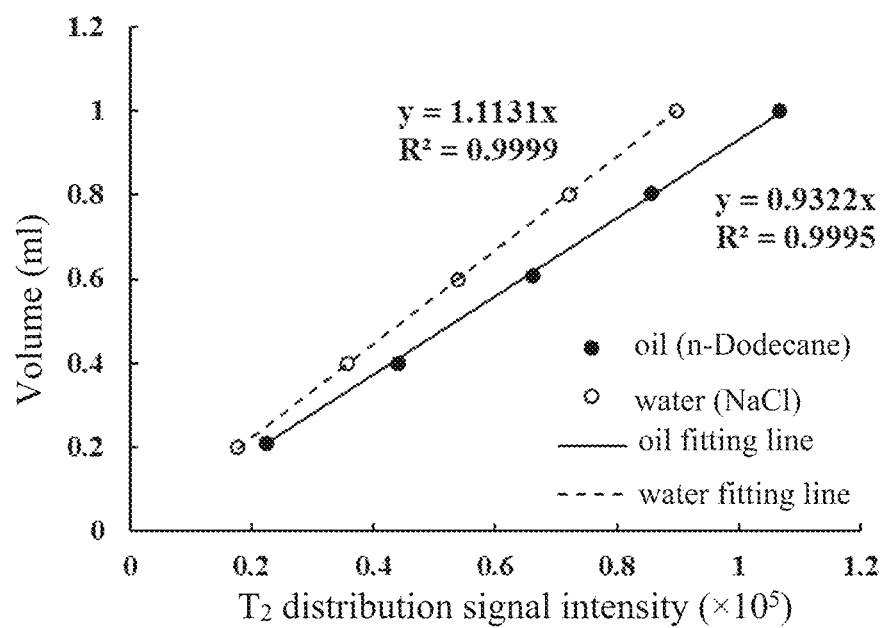
FIG. 7 is a calibration diagram of NMR signals of the free/bulk oil and the free/bulk water according to the present invention.

As shown in FIG. 7, according to the relationship between the NMR $T_2$ distribution area and the volume of free/bulk oil and free/bulk water with different volumes, it is obtained that $k_1=0.9322$ and $k_2=1.1131$; the relationship between the NMR signal intensity and the volume of the free/bulk oil/water (formulas (1)-(2)) is for calculation of the volume of free/bulk oil and free/bulk water in the pores of the organic-rich shale.

2) Calibrating NMR signal intensity and mass of adsorbed oil Crushing the above dry shale sample to 80-100 meshes; then placing into the vacuum pressurization saturation device, and vacuumizing for 24 hours, wherein the vacuum degree is $1\times10^4$ Pa; after finishing vacuumizing, processing the powdery dry shale sample with pressurization and oil saturation, wherein the pressurization saturation time is 36 hours.

Heating the powdery dry shale sample after being saturated with oil with a constant temperature, wherein the heating temperature is 50° C.; weighing samples of different heating time periods, processing with the NMR $T_2$ distribution test, and recording changes of the sample mass and the NMR $T_2$ distribution, wherein: when the sample mass and the NMR $T_2$ distribution is stable, it is considered that the dry shale sample with adsorbed oil is obtained; the current sample mass $m_a$ is recorded, and the NMR $T_2$ distribution signal intensity thereof is $T_{2a}$; heating the dry shale sample with adsorbed oil with a temperature of 315° C. for 48 hours, and obtaining the dry shale sample, wherein the current sample mass is recorded to be $m_0$, and the current NMR $T_2$ distribution signal intensity of the dry shale sample is $T_{20}$.

Processing different dry shale samples as above; fitting the relationships between the mass ($m_a-m_0$) and the NMR signal intensity ($T_{2a}-T_{20}$) of the adsorbed oil; and obtaining a calibration formula between the NMR signal intensity and the mass of the adsorbed oil that:

$$m_{a0}=k_a \times A_{a0} \quad (3);$$

wherein: in the formula (3), $m_a$ is mass of the adsorbed oil, in unit of mg; $A_{ao}$ is an NMR $T_2$ distribution area of the adsorbed oil, in unit of a.u.; and $k_a$ is a conversion coefficient between the NMR signal intensity and the mass of the adsorbed oil.

Figure 8:
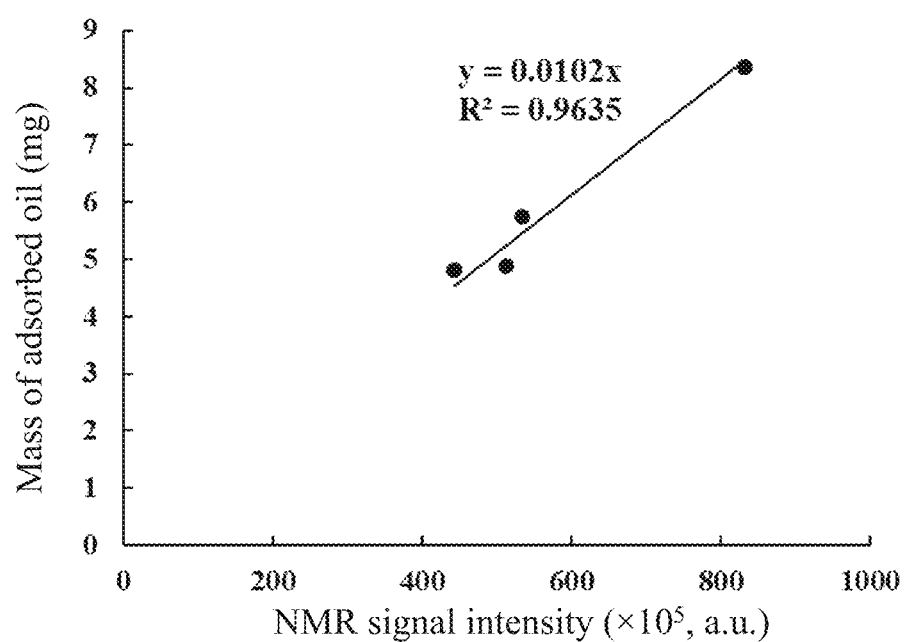
FIG. 8 is a relationship diagram between an NMR signal intensity and mass of adsorbed oil according to the present invention.

As shown in FIG. 8, according to the relationships between the NMR $T_2$ distribution area and the mass of adsorbed oil of different samples, it is obtained that $k_a=0.0102$. The relationship between the NMR signal intensity and the mass of the adsorbed oil (formula (3)) is for calculation of the mass of the adsorbed oil in the pores of the organic-rich shale.

3) Calculating Fluid Content in Organic-Rich Shale

According to the NMR $T_1$-$T_2$ map test results of shale, the classification scheme for the signals of the NMR $T_1$-$T_2$ maps of shale is established; the organic matter signal intensities are extracted from the NMR $T_1$-$T_2$ map, and contrasted with the pyrolysis experiment; the NMR signal intensities of free oil and free water are extracted from the NMR $T_1$-$T_2$ map, and the volumes of free oil and free water in the pores are respectively obtained through the formulas (1) and (2); combined with the sample porosity, the oil/water saturation value of shale is estimated; the NMR signal intensity of adsorbed oil is extracted from the NMR $T_1$-$T_2$ map, and with the formula (3), the content of adsorbed oil in the organic-rich shale is obtained.

The evaluation for the porosity of the organic-rich shale is further described as follows.

Evaluation for Porosity of Organic-Rich Shale

In the evaluation of the porosity of the organic-rich shale, according to the differences between the NMR $T_2$ distributions of the dry shale sample and the oil-saturated shale sample, with the $T_2$ distribution of the organic-rich shale after being saturated with oil as the target and the $T_2$ distribution of the dry shale sample as the basement, subtracting the basement, and obtaining the $T_2$ distribution of oil in the pores; and, based on the $T_2$ distribution of oil in the pores, combined with the relationship between the NMR signal intensity and the volume of oil (formula (1)), evaluating the porosity of the organic-rich shale. Detailed technical solutions are described as follows.

(1) Preparation of Dry Shale Sample

For the original shale taken back from the core library, because of the adsorption effect of rock mineral/kerogen and the accommodation effect of small pores, some water and oil which is relatively heavy are still remained in the pores. Therefore, if want to directly perform the helium porosity test and the pressurization saturation fluid processing, there mainly exist following problems. Firstly, the residual water and oil occupy the volume of pores, causing that the porosity obtained by the helium porosity test is smaller than the actual porosity. Secondly, the fluid-saturated shale sample is not saturated with the single fluid; the response features of the NMR signals of different fluids are different, and it will generate an error during conversion between the NMR signal and the fluid volume, resulting in the distortion of porosity. Thus, it is required to process the original shale with oil washing/extracting and drying.

The preparation process of the dry shale sample has been illustrated in detail at the preparation of the shales of different oil-containing and water-containing conditions, and thus is not repeated herein.

The dry shale sample after processing is made with the NMR $T_1$-$T_2$ map test, for checking whether the residual oil and water are completely removed from the dry shale sample after extraction and drying. As shown in FIG. 4, compared with the shale, only the solid organic matter (kerogen) signal ($T_1/T_2>100$, $T_2<1$ ms) and the mineral structural water signal ($T_1/T_2<100$, $T_2<0.2$ ms) are remained in the NMR $T_1$-$T_2$ map of the dry shale sample, and the residual oil signal and water signal disappear ($T_2>1$ ms). If the NMR $T_1$-$T_2$ map signals of residual oil and water do not disappear, it is required to process the shale with extraction and drying again.

The dry shale sample is processed with the NMR $T_2$ distribution test, and the NMR $T_2$ decay curve (S(t, dry)) of the dry shale sample is obtained.

(2) NMR Porosity Calculation

1) Helium Porosity Measurement

Placing the regular columnar dry shale sample (with a diameter of 2.5 cm) into the overburden pressure porosity and permeability measurement device, introducing helium into the device, and performing the helium porosity test in the common way, wherein the test process refers to the petroleum and natural gas industry standard, SY/T 6485-1999 *Measurement method for porosity and permeability of rock under overburden pressure*.

2) Pressurization and Oil Saturation Experiment of Dry Shale Sample

Figure 9:
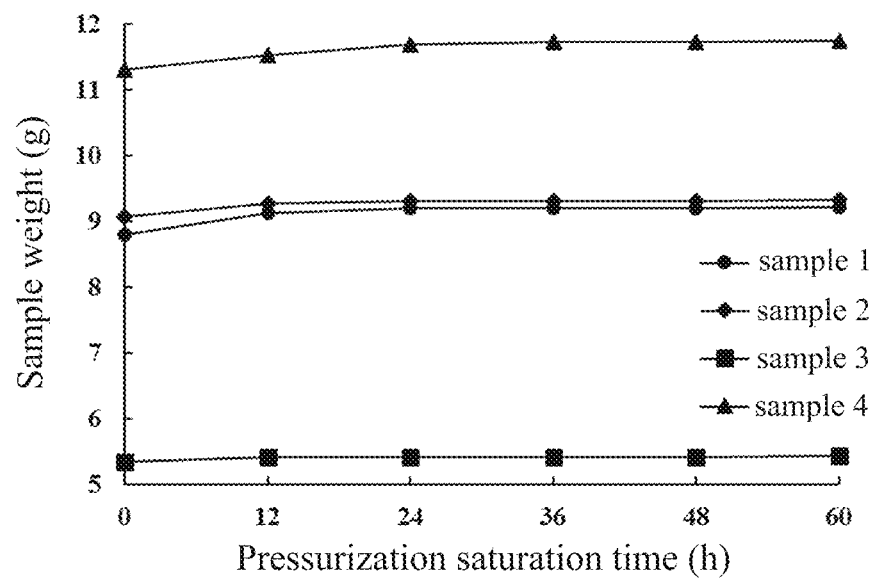
FIG. 9 is a weight change curve diagram of samples tested at different pressurization saturation time periods according to the present invention.

In order to eliminate the hydration influence of water saturation on the shale sample, processing the dry shale sample after extraction and drying with pressurization and oil saturation, particularly comprising steps of: placing the dry shale sample into the vacuum pressurization saturation device; vacuumizing the dry shale sample for 24 hours with a vacuum degree of $1\times10^{-4}$ Pa; after finishing vacuumizing, processing the dry shale sample with pressurization and oil saturation (with the example of n-dodecane, similarly hereinafter) for 60 hours, wherein a pressurization saturation pressure is 20 MPa; weighing the oil-saturated shale sample at different pressurization saturation time periods (12 hours, 24 hours, 36 hours, 48 hours and 60 hours); and, when the weight is stable (the change range of weights measured at two adjacent time periods is lower than 1%), obtaining the 100% oil-saturated shale sample. FIG. 9 is weight change curves of four samples tested at different pressurization saturation time periods, wherein: when the pressurization saturation time reaches 36 hours, the sample weight becomes stable, and it is considered that the 100% oil-saturated shale sample is obtained.

Figure 10:
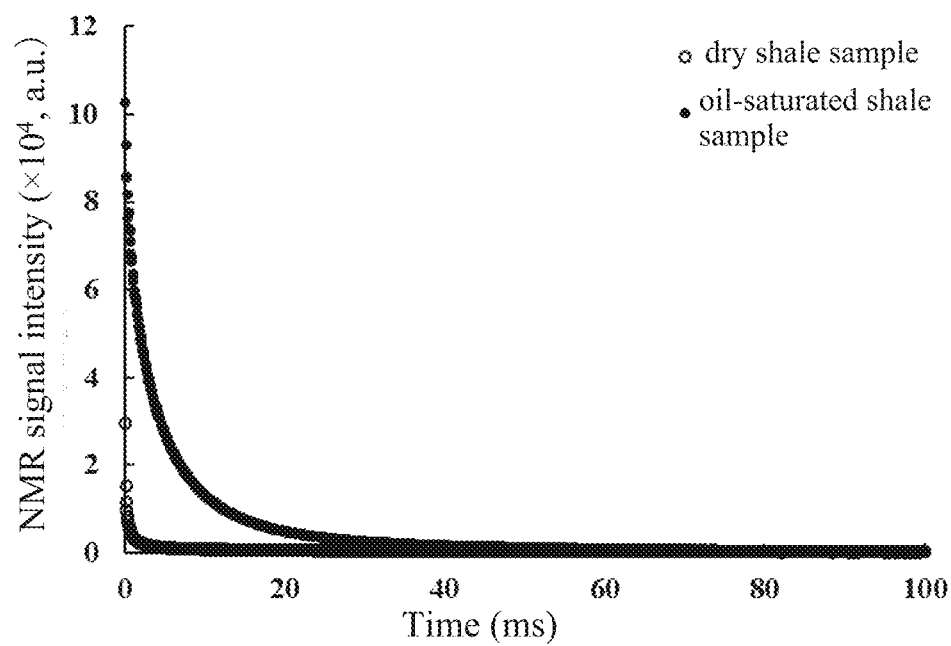
FIG. 10 is a comparison diagram between NMR $T_2$ decay curves of the organic-rich dry shale sample and the oil-saturated shale sample according to the present invention.

3) Acquirement of NMR $T_2$ Distribution of Saturating Oil and Calculation of Porosity Under the premise that the NMR test parameters of the oil-saturated shale sample are consistent with that of the dry shale sample, processing the oil-saturated shale sample with the NMR $T_2$ distribution test, and obtaining the NMR $T_2$ decay curve (S(t, sat)) of the oil-saturated shale sample, as shown in FIG. 10. Therefore, through subtracting the NMR $T_2$ decay curve (S(t, dry)) of the dry shale sample from the NMR $T_2$ decay curve (S(t, sat)) of the oil-saturated shale sample, the $T_2$ decay curve ($\Delta S(t, oil)$) of saturating oil is obtained that:

$$S(t, dry) = \sum_i A_i \exp\left(-\frac{t}{T_{2i}}\right); \quad (4)$$

$$S(t, sat) = \sum_j A_j \exp\left(-\frac{t}{T_{2j}}\right); \quad (5)$$

$$\Delta S(t, oil) = S(t, sat) - S(t, dry) \quad (6)$$
$$= \sum_k \Delta A_k \exp\left(-\frac{t}{T_{2k}}\right);$$

wherein: in the formulas (4)-(6), S(t, dry) is an echo amplitude of the dry shale sample; S(t, sat) is an echo amplitude of the oil-saturated shale sample; $\Delta S(t, oil)$ is an echo amplitude of saturating oil; $A_i$ is an amplitude of the dry shale sample when $T_2=T_{2i}$; $A_j$ is an amplitude of the oil-saturated shale sample when $T_2=T_{2j}$; $\Delta A_k$ is an amplitude of saturating oil when $T_2=T_{2k}$; t=n*TE, wherein n is number of echoes; i, j and k respectively represent orders of signal collection points, with a value of 1, 2, 3 . . . n.

Figure 11:
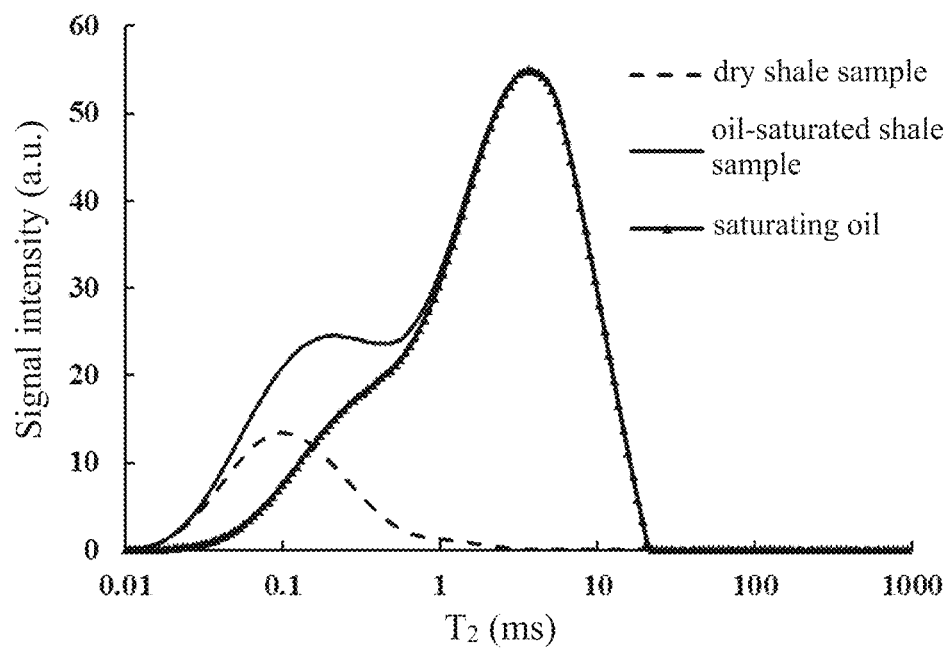
FIG. 11 is a comparison diagram between NMR $T_2$ distributions of dry shale sample, oil-saturated shale sample, and saturating oil according to the present invention.

According to the $T_2$ decay curve $\Delta S(t, oil)$ of saturating oil, through mathematical subtracting, the $T_2$ distribution of oil in the shale sample is obtained. As shown in FIG. 11, the NMR signals of the dry shale sample mainly come from the solid organic matter (kerogen) and clay mineral structural water, wherein the relaxation time thereof is relatively short and $T_2$ is distributed between 0.01-1 ms in form of single peak. After being saturated with oil, two peaks occur in the NMR $T_2$ distribution, wherein: the front peak keeps the form of dry shale sample, and only the signal intensity is increased; and, because of the influence of the pore size, the change amplitude of the front peak is far smaller than that of the rear peak. For the $T_2$ distribution of saturating oil evaluated by the present invention, compared with the $T_2$ distribution of the oil-saturated shale sample, the rear peak is much the same; the signal intensity at the front peak is lower, and the reduced signal is namely the signals of solid organic matter and clay mineral structural water in the dry shale sample.

According to the NMR $T_2$ distribution curve of saturating oil, the $T_2$ distribution area of saturating oil is calculated; combined with the calibration formula (formula (1)) between the volume and the NMR signal of free oil, the volume of saturating oil is calculated, namely the pore volume of the shale sample; and the porosity is obtained through dividing the sample volume by the pore volume. The porosity of the organic-rich shale obtained by the NMR method is contrasted with the porosity tested by the helium method, so as to verify the accuracy and feasibility of the method.

The present invention is further illustrated with the NMR characterization method for the pore size distribution of the organic-rich shale.

NMR Characterization Method for Pore Size Distribution of Organic-Rich Shale

In the pore size characterization and evaluation of the organic-rich shale, according to the differences between the NMR $T_2$ distributions of dry shale sample and oil-saturated shale sample, with the $T_2$ distribution of the organic-rich shale after being saturated with oil as the target and the $T_2$ distribution of the dry shale sample as the basement, the $T_2$ distribution of oil in the pores is obtained through subtracting the basement; and, based on the $T_2$ distribution of oil in the pores, combined with experiments for pore size characterization of dry shale sample, such as low-temperature nitrogen adsorption, high-pressure mercury injection and large-area high-resolution electron microscope imaging, the NMR characterization method for the pore size distribution of the organic-rich shale is established.

Figure 12:
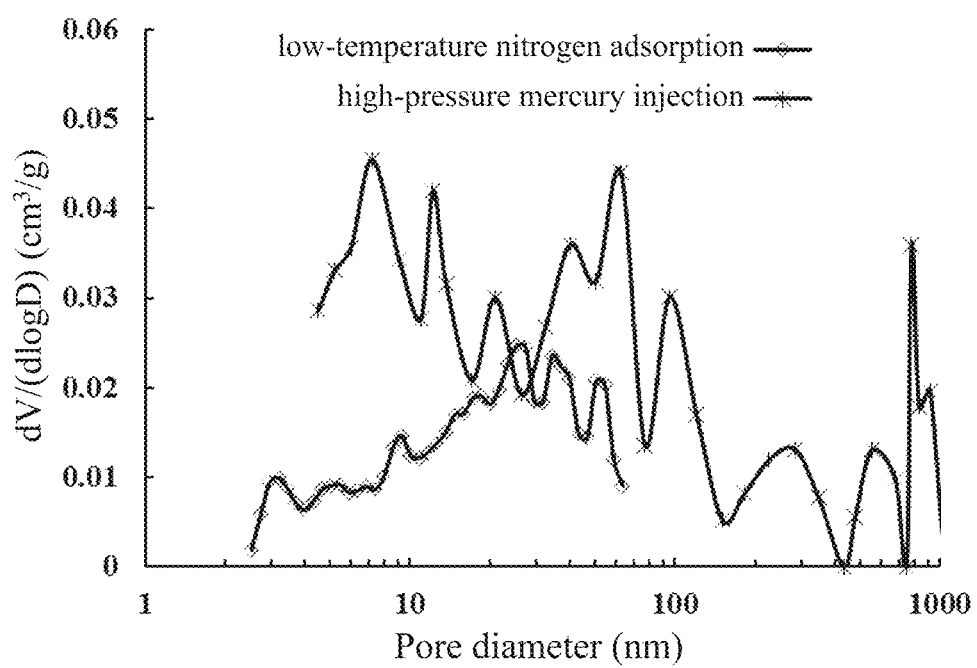
FIG. 12 is a comparison diagram between pore size distributions of the organic-rich dry shale sample, obtained respectively by low-temperature nitrogen adsorption and high-pressure mercury injection, according to the present invention.

(1) Low-Temperature Nitrogen Adsorption and High-Pressure Mercury Injection Experiments Cutting and crushing the dry shale sample; firstly preparing into a sample with length, width and height of 1 cm 1 cm 1 cm, and performing the high-pressure mercury injection test (400 Mpa); according to the Washburn model, obtaining the pore size distribution curve $R_{MICP}$ of the pores with a diameter larger than 7.2 nm (with a horizontal axis of pore diameter and a vertical axis of dV/(dlogD), similarly hereinafter), wherein the operation process refers to the industry standard of SY/T 5346-2005; utilizing the powdered sample (80-100 meshes) after uniformly mixing, and performing the low-temperature nitrogen adsorption experiment; according to the BJH adsorption isotherm, obtaining the pore size distribution curve $R_{LTNA}$ of the pores with a diameter smaller than 100 nm, as shown in FIG. 12, wherein the operation process refers to the industry standard of GB/T 19587-2004.

(2) Large-Area High-Resolution Electron Microscope Imaging Experiment

Figure 13:
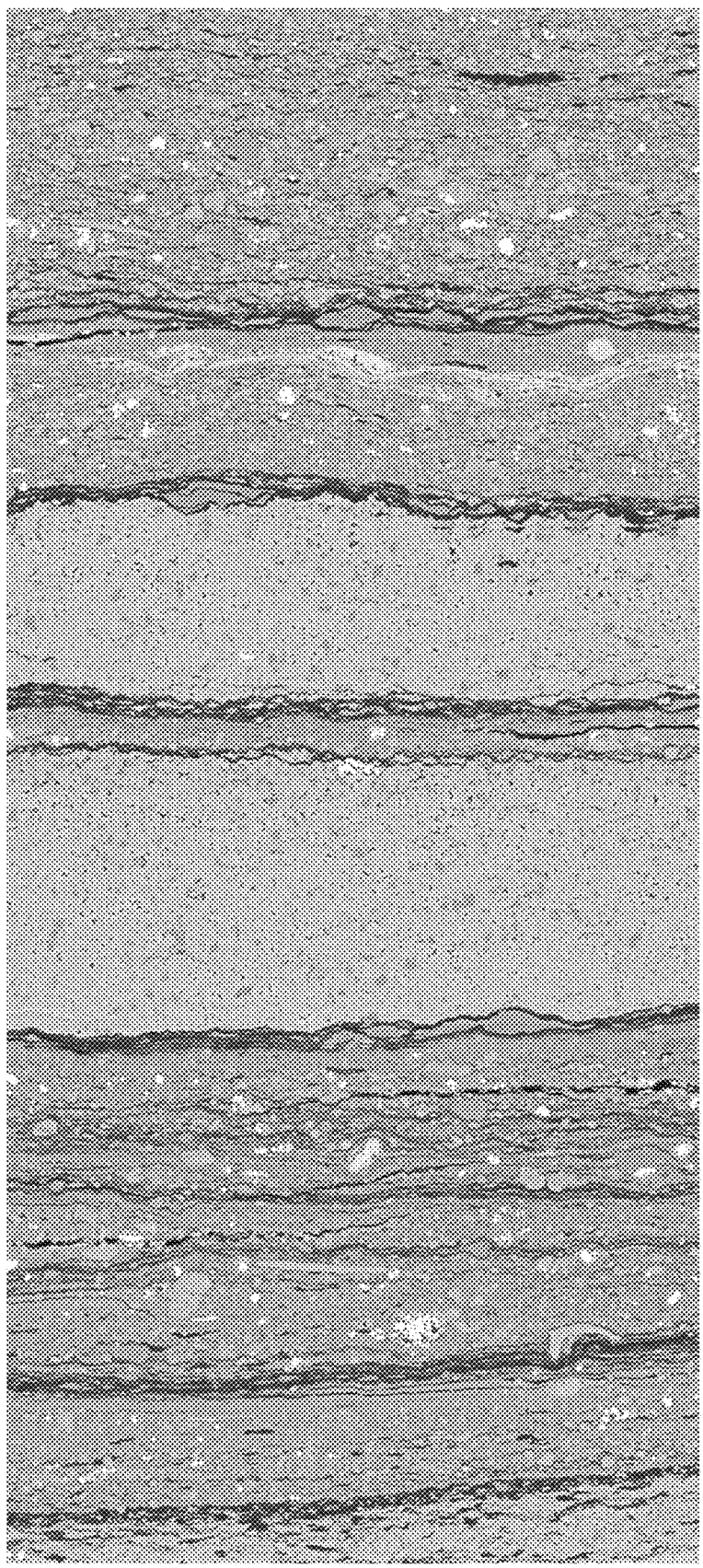
FIG. 13 is a photo of the organic-rich shale by large-area high-resolution electron microscope imaging according to the present invention.

Processing the surface of the vertical bedding of the regular sample block (1 cm×1 cm×1 cm) with mechanical polishing by the precise cutting-grinding integrated machine; fixing the sample after mechanical polishing on the aluminum T-shaped sample stage by the paraffin, polishing for 20 minutes at conditions of 5 KV and 2 mA with the argon ion polishing machine, then polishing at conditions of 2 KV and 2 mA for 10 minutes, alternately repeating for four times, and finishing polishing of the sample surface, wherein an included angle between the polished surface and the argon ion beam is 3°. In order to solve the problems of small vision filed of scanning electron microscope and heterogeneous sample, the present invention adopts the large-area high-resolution electron microscope imaging technology (AMICSCAN), for imaging of the polished surface of the sample at the low voltage of 1.2-0.8 KV and the low current of 200-80 pA, wherein the area of the imaging vision field is 300 um×800 um, as shown in FIG. 13. The pores are extracted through the threshold division method, the pore area is obtained, and the curve diagram of pore area verse pore diameter (dS/(dlogD)) is graphed.

(3) Determining Calibration Coefficient C

The pore size distribution curve of the present invention adopts the horizontal axis of pore diameter (width) and the vertical axis of dV/(dlogD), wherein the physical meaning of the vertical axis indicates the pore number corresponding to a certain pore diameter.

Superimposing the pore size distribution curve $R_{MICP}$ of high-pressure mercury injection with the pore size distribution curve $R_{LTNA}$ of low-temperature nitrogen adsorption; selecting a connection pore diameter $r_p$ at a pore diameter range of 10-100 nm, wherein dV/(d log D) values of two pore size distribution curves at the point of connection pore diameter $r_p$ are required to be roughly the same, ensuring that the pore number measured by the low-temperature nitrogen adsorption method and the high-pressure mercury injection method is almost identical at the pore diameter $r_p$; remaining data points which are smaller than $r_p$ in the low-temperature nitrogen adsorption method and larger than $r_p$ in the high-pressure mercury injection method, and constructing the full pore size distribution curve $R_{LTNA\text{-}MICP}$ of the shale.

According to the formula (1), converting the signal intensities corresponding to every $T_2$ point in the NMR $T_2$ distribution of saturating oil (FIG. 11) into the pore volumes; and, with a specified calibration coefficient C, converting the $T_2$ relaxation time to the pore diameter through a formula of:

$$d = C \times T_2 \quad (7);$$

wherein: in the formula (7), d is the pore diameter, in unit of nm; $T_2$ is the NMR transverse relaxation time, in unit of ms; and C is the calibration coefficient;

with the horizontal axis of pore diameter and the vertical axis of dV/(dlogD), graphing a pore size distribution curve $R_{NMR}$ converted from the NMR $T_2$ distribution of the saturating oil; superimposing curves of $R_{LTNA\text{-}MICP}$ and $R_{NMR}$, and calculating an error value thereof through a formula of:

$$Q = \frac{1}{n}\sum_{i=1}^{n} \sqrt{(R_{LTNA-MICP-i} - R_{NMR-i})^2} \quad (8)$$

$$= \frac{1}{n}\sum_{i=1}^{n} \sqrt{(R_{LTNA-MICP-i} - C \times T_{2i})^2};$$

wherein: in the formula (8), Q is the error value; n is a number of data points in the $R_{LTNA\text{-}MICP}$ pore size distribution curve; $R_{LTNA\text{-}MICP\text{-}i}$ is an $i^{th}$ data point in the $R_{LTNA\text{-}MICP}$ pore size distribution curve; and $R_{NMR\text{-}i}$ is $R_{NMR}$ data corresponding to the $i^{th}$ data point in the $R_{LTNA\text{-}MICP}$ pore size distribution curve;

when similarity of the curves of $R_{LTNA\text{-}MICP}$ and $R_{NMR}$ is closest, namely the error value is smallest, recording a current value of the calibration coefficient C as a pore diameter calibration coefficient value of the NMR transverse relaxation time.

Combined with the large-area high-resolution electron microscope imaging experiment, through analyzing and contrasting the NMR pore diameter conversion results calibrated by the low-temperature nitrogen adsorption and the high-pressure mercury injection with the curve diagram of pore area verse the pore diameter (dS/(dlogD)) obtained by the large-area high-resolution electron microscope imaging, the effect of NMR pore diameter calibration is verified.

The present invention is further described combined with effects as follows.

Figure 14:
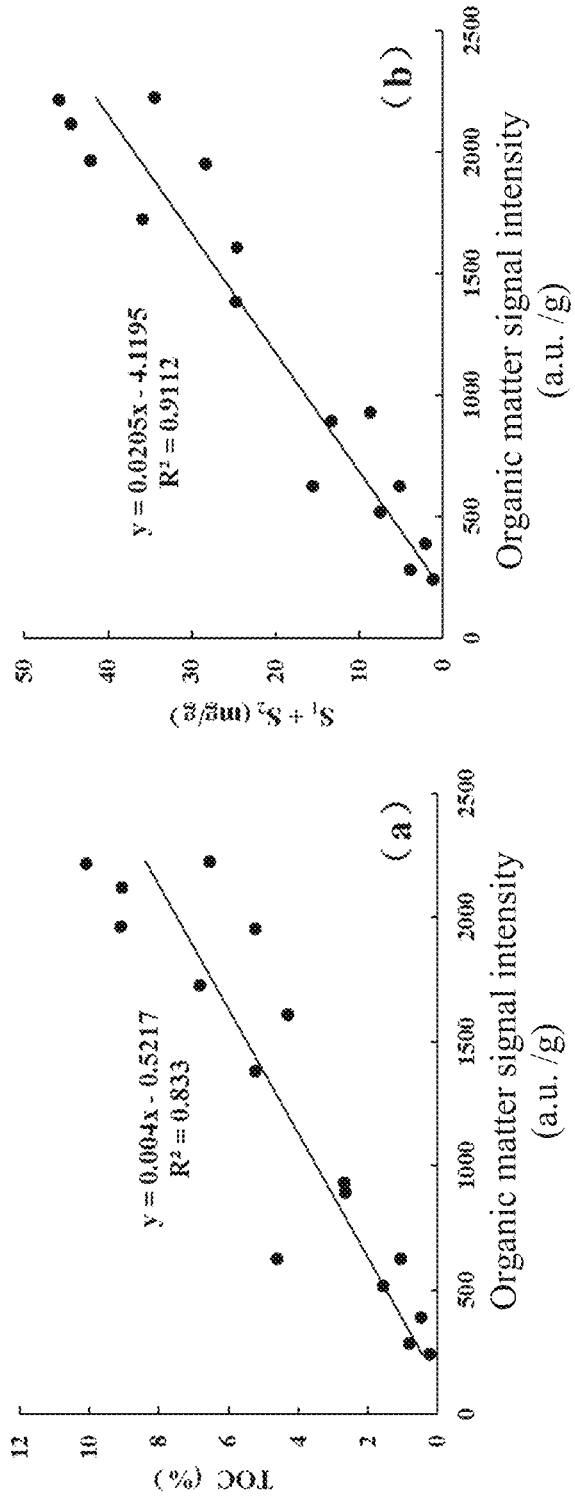
FIG. 14 is a relationship diagram between an organic matter NMR signal intensity of the organic-rich shale and geochemical parameters according to the present invention.
Figure 15:
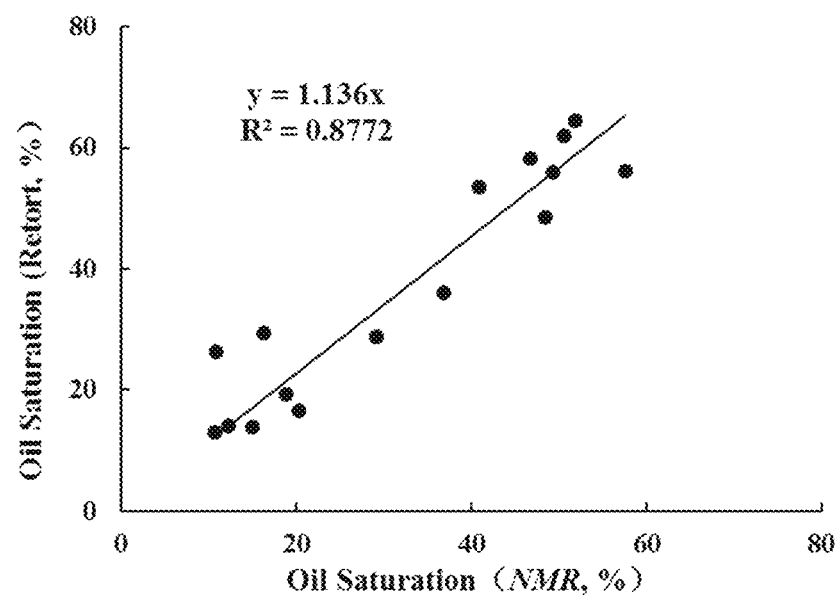
FIG. 15 is an NMR evaluation result diagram of oil saturation of the organic-rich shale according to the present invention.
Figure 16:
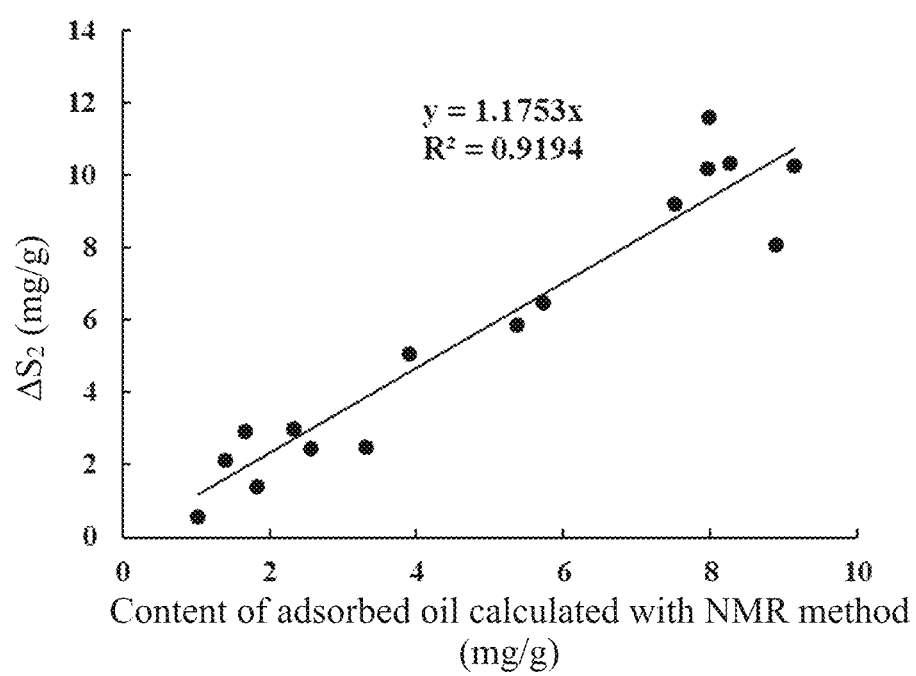
FIG. 16 is an NMR evaluation result diagram of the content of the adsorbed oil in the organic-rich shale according to the present invention.

In the hydrogen-bearing component identification and fluid quantitative characterization of the organic-rich shale, the present invention takes 16 shale samples from Shahejie formation in Damintun Sag of Bohai Bay Basin, China as examples. Based on the above signal classification scheme for each hydrogen-bearing component in the shale and the quantitative characterization method for the fluid content in the organic-rich shale, the organic matter signal intensity of every sample is extracted from the $T_1$-$T_2$ map, and contrasted with the organic geochemical parameters (TOC, S1 and S2), as shown in FIG. 14. The organic matter signal intensity by the NMR test shows relatively good linear positive correlation with the parameters of TOC and S1+S2, further proving the feasibility of the classification scheme for each hydrogen-bearing component in the shale. Moreover, according to the present invention, the signal intensities of free oil and free water are respectively extracted from the $T_1$-$T_2$ maps; with utilizing the calibration relationships between the NMR signal intensity and the volume of free oil/water (formulas (1) and (2)), the volumes of free oil and free water are calculated; and, combined with the porosity measured by the NMR, the oil saturation and water saturation of shale are respectively estimated. With the oil saturation as the example, as shown in FIG. 15, the evaluation results of oil saturation of the present invention are roughly the same as that of the retort method. Meanwhile, the present invention extracts the signal intensity of adsorbed oil from the $T_1$-$T_2$ maps, and then the mass of adsorbed oil is estimated with utilizing the relationship between the NMR signal intensity and the mass of adsorbed oil (formula (3)). As shown in FIG. 16, the content of adsorbed oil shows a good relationship with the change $\Delta S_2$ (indicating the heavy oil) of the pyrolysis parameter S2 before and after oil extracting of the organic-rich shale.

Figure 17:
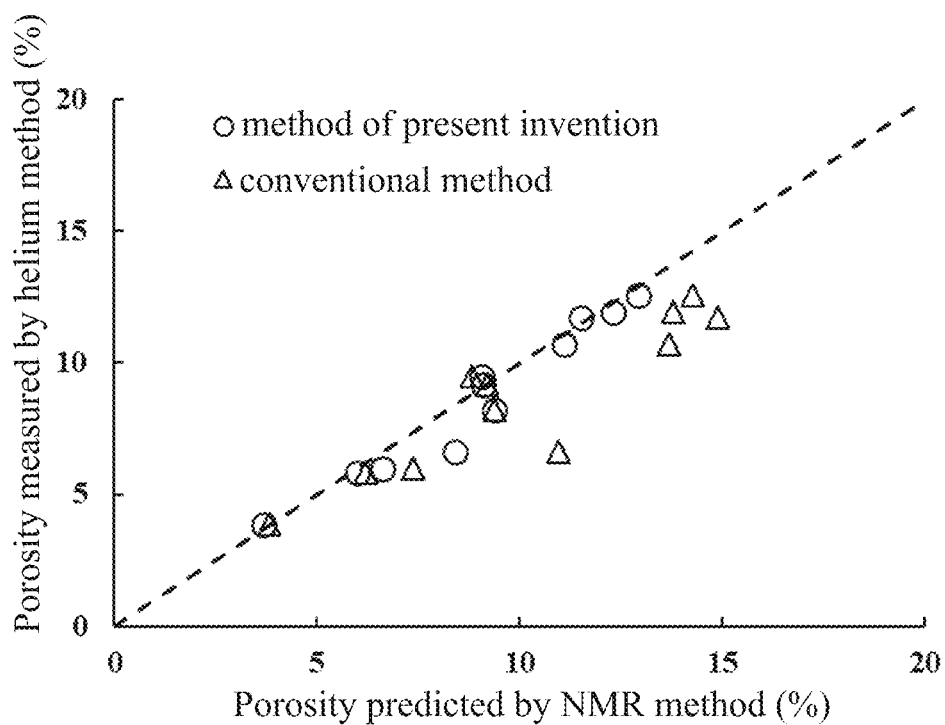
FIG. 17 is an NMR evaluation result diagram of the porosity of the organic-rich shale according to the present invention.

In the porosity evaluation of the organic-rich shale, the present invention takes 11 shales from Shahejie formation in Damintun Sag of Bohai Bay Basin, China as the examples. According to the above NMR measurement method for the porosity of the organic-rich shale, as shown in FIG. 17, compared with the helium porosity data, the porosity predicted by the $T_2$ distribution of saturating oil of the present invention and the porosity by the helium method are uniformly distributed at two sides of the diagonal. Moreover, for the porosity which is obtained through the direct calculation of the oil-saturated organic-rich shale sample without removing the signal of dry shale sample (e.g., solid organic matter and mineral structural water), the conventional test results are generally higher than the porosity tested by the helium method; the porosity calculated through the NMR $T_2$ distribution after removing the signal of dry shale sample by the present invention is closer to the test results by the helium method, having a higher reliability.

Figure 18:
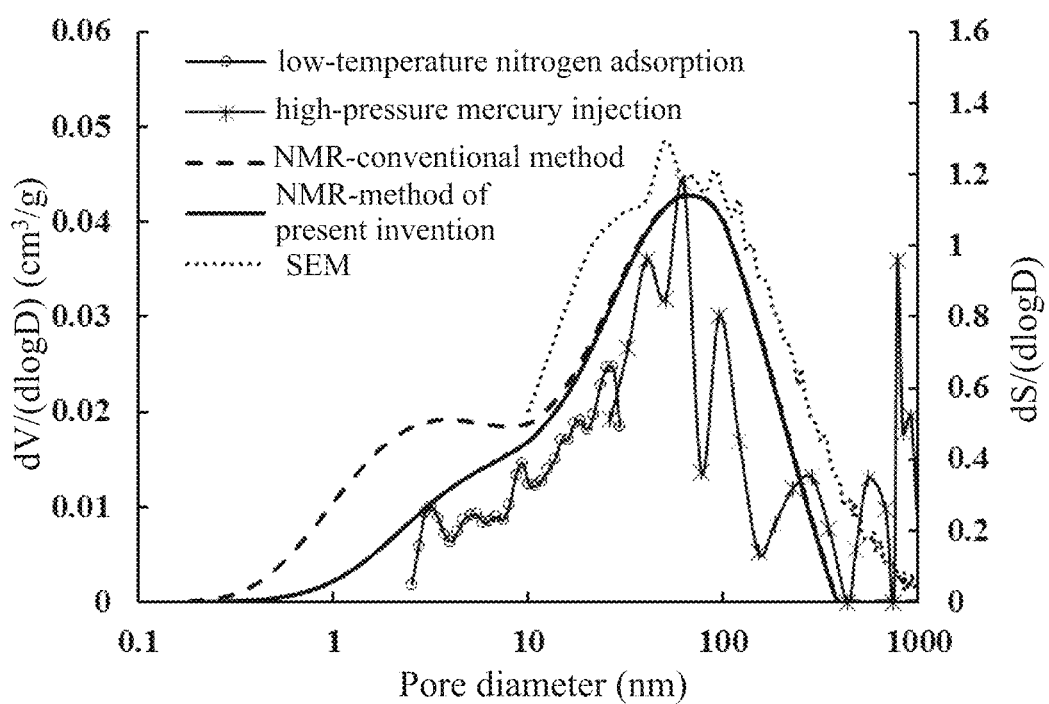
FIG. 18 is an NMR characterization result diagram of the pore size distribution of the organic-rich shale according to the present invention.

In the characterization of pore size distribution of the organic-rich shale, the present invention takes the shale examples from Shahejie formation in Dongying Sag of Bohai Bay Basin, China as the examples. According to the above NMR characterization method for the pore size distribution of the organic-rich shale, the conversion coefficient of the NMR $T_2$ time is calibrated together with the low-temperature nitrogen adsorption method and the high-pressure mercury injection method, as shown in FIG. 18. With the horizontal axis of pore width (diameter) and the vertical axis of dV/(dlogD), the connection point of the low-temperature nitrogen adsorption $R_{LTNA}$ curve and the high-pressure mercury injection $R_{MICP}$ curve is 25 nm; when the pore diameter smaller than 25 nm, the low-temperature nitrogen adsorption $R_{LTNA}$ curve is utilized; when the pore diameter larger than 25 nm, the high-pressure mercury injection $R_{MICP}$ curve is utilized, and the curve $R_{LTNA\text{-}MICP}$ is constructed. Through superimposing the curves of $R_{LTNA\text{-}MICP}$ and $R_{NMR}$, when the error value of two curves is smallest, the conversion coefficient C of the NMR $T_2$ time is calibrated to be 18. Compared with utilizing the curve diagram of pore area verse the pore diameter (dS/(dlogD)) obtained by the large-area high-resolution electron microscope imaging technology (AMICSCAN), the $R_{NMR}$ is closer in trend, further proving the reliability of the conversion coefficient calibrated together with the low-temperature nitrogen adsorption method and the high-pressure mercury injection method by the present invention. Additionally, compared with the pore size distribution results based on the NMR $T_2$ distribution of oil-saturated shale sample, the pore diameter conversion results obtained through directly utilizing the NMR $T_2$ distribution of saturating oil (obtained through subtracting the dry shale sample basement from the oil-saturated shale sample) by the present invention shows the high consistency with the low-temperature nitrogen adsorption experimental results in the small pores (<10 nm), which highlights the innovation of the present invention in the organic-rich shale's pore size distribution characterized by the NMR technique.

The identification and quantitative characterization for hydrogen-bearing components and the evaluation for porosity and pore size distribution of the organic-rich shale have great significance in the exploration of shale oil and gas. Conventionally, in view of the deeper microscope research of the organic-rich shale reservoir and the accuracy improvement of the NMR device, the present invention utilizes the low echo time (TE=0.07 ms), considers the complexity of hydrogen-bearing components in the shale, establishes the classification scheme for each hydrogen-bearing component in the shale according to the differences among the NMR $T_1$-$T_2$ maps of kerogen, oil-adsorbed kerogen, clay minerals of different water-containing conditions, shale, dry shale sample, oil-saturated shale sample and water-saturated shale sample, and proposes the identification and quantitative characterization method for the hydrogen-bearing components in the organic-rich shale based on the NMR $T_1$-$T_2$ map. With considering the relatively high NMR signal intensity of the organic-rich dry shale sample (enriched in organic matters and mineral structural water), the present invention adopts the $T_2$ distribution of the organic-rich shale after being saturated with oil as the target and the $T_2$ distribution of the dry shale sample as the basement, obtains the $T_2$ distribution of oil in the pores through subtracting the basement, and evaluates the porosity and pore size distribution of the organic-rich shale based on the $T_2$ distribution of oil in the pores. The present invention provides the identification and quantitative characterization method for the hydrogen-bearing components and the evaluation method for the porosity and the pore size distribution of the organic-rich shale based on the NMR, which shows relatively high innovation and reliability in comparison with the conventional method. Therefore, the present invention is beneficial to perfecting the analysis of NMR in shale petrophysical measurement.

The above-described is only the preferred embodiment of the present invention, not for limiting the present invention. Modifications, equivalent replacements, and improvements made within the spirit and principle of the present invention are all encompassed in the protection scope of the present invention.

What is claimed is:

1. An evaluation method for hydrogen-bearing components, porosity and pore size distribution of organic-rich shale, comprising steps of:
   according to differences among NMR (nuclear magnetic resonance) $T_1$-$T_2$ maps of kerogen, oil-adsorbed kerogen, clay minerals of different water-containing conditions, shale, dry shale sample, oil-saturated shale sample and water-saturated shale sample, establishing a classification scheme for each hydrogen-hearing component and a quantitative characterization method for fluid components of the organic-rich shale; and
   because NMR signals of organic matters and clay mineral structural water exist in the organic-rich dry shale sample, with a $T_2$ distribution of the organic-rich shale after being saturated with oil as a target and a $T_2$ distribution of the dry shale sample as a basement, subtracting the basement, and obtaining a $T_2$ distribution of oil in pores; and, based on the $T_2$ distribution of oil in the pores, evaluating the porosity and the pore size distribution of the organic-rich shale.

2. The evaluation method for the hydrogen-bearing components, the porosity and the pore size distribution of the organic-rich shale, as recited in claim 1, particularly comprising steps of:
   through contrastive analysis of the NMR $T_1$-$T_2$ maps of kerogen, oil-adsorbed kerogen, clay minerals of different water-containing conditions, and organic-rich shales of different oil-containing/water-containing conditions, determining relaxation features of each hydrogen-bearing component, and establishing the classification scheme for signals of each hydrogen-bearing component and the quantitative characterization method for the fluid components of the organic-rich shale;
   processing the organic-rich shale with oil extracting and drying, and obtaining the dry shale sample; dividing the dry shale sample into two parts, wherein one part is processed with pressurization and oil saturation for an NMR experiment, and the other part is for experiments of porosity with a helium method, low temperature nitrogen adsorption, high-pressure mercury injection, and scanning electron microscope; and
   with the $T_2$ distribution of the organic-rich shale after being saturated with oil as the target and the $T_2$ distribution of the dry shale sample as the basement, subtracting the basement, and obtaining the $T_2$ distribution of oil in the pores; based on the $T_2$ distribution of oil in the pores, combined with a relationship between an NMR signal intensity and a volume of oil, evaluating the porosity of the organic-rich shale; and, combined with the experiments of low temperature nitrogen adsorption, high-pressure mercury injection, and scanning electron microscope, establishing an NMR characterization method for the pore size distribution of the organic-rich shale.

3. The evaluation method for the hydrogen-bearing components, the porosity and the pore size distribution of the organic-rich shale, as recited in claim 2, wherein:
the kerogen and the oil-adsorbed kerogen are prepared through steps of:
crushing an organic-rich shale sample to above 100 meshes; immersing in distilled water for 4 hours; successively processing with an acid treatment, an alkali treatment, and a pyrite treatment; thereafter adding dichloromethane, and stirring; after the dichloromethane is volatilized, obtaining the oil-adsorbed kerogen; processing the oil-adsorbed kerogen with chloroform extraction for 24 hours, and obtaining the kerogen;
the clay minerals of different water-containing conditions are prepared through steps of:
firstly saturating the clay mineral with water, and then drying for 24 hours respectively at 121° C. and 315° C., wherein: under a water saturation condition, a free water-containing clay mineral is obtained; after drying at 121° C. for 24 hours, an adsorbed water-containing clay mineral is obtained; and, after drying at 315° C. for 24 hours, a clay mineral merely containing structural water is obtained; and
the organic-rich shales of different oil-containing/water-containing conditions are prepared through steps of:
firstly processing an as-received shale sample with chloroform extraction for 24 hours; then extracting the shale sample after chloroform extraction with a ternary organic solution MAB having a relatively strong polarity for 24 hours, wherein a ratio of methyl alcohol, acetone and benzene in the tenary organic solution MAB is 15:15:70, so as to remove residual oil in the pores of the shale as far as possible; after ternary extraction, processing the shale sample with a high-temperature drying experiment until reaching a constant weight, wherein a drying temperature is set to he 315° C. and kept for 24 hours, so as to remove residual free water in the pores of the shale and residual bound/adsorbed water at surfaces of the pores, thereby obtaining the dry shale sample; and preserving the dry shale sample in a dryer at a room temperature.

4. The evaluation method for the hydrogen-bearing components, the porosity and the pore size distribution of the organic-rich shale, as recited in claim 2, wherein:
the quantitative characterization method for the fluid components in the organic-rich shale comprises steps of:
1) calibrating an NMR signal intensity and a volume of free/bulk oil/water, particularly comprising steps of:
configuring standard samples of oil and water with different volumes of 0.2 ml, 0.4 ml, 0.6 ml, 0.8 ml and 1.0 ml, and respectively processing with an NMR $T_2$ distribution test; according to the volume and a corresponding NMR $T_2$ distribution area of the free/bulk oil/water, establishing calibration formulas between the NMR signal intensity and the volume of the free/bulk oil and water that:

$$V_O = k_1 \times A_O \quad (1)$$

$$V_w = k_2 \times A_w \quad (2)$$

wherein: in the formulas, $V_O$ is the volume of the free/bulk oil, and $V_w$ is the volume of the free/bulk water, both in unit of ml; $A_O$ is the NMR $T_2$ distribution area of the free/bulk oil, and $A_w$ is the NMR $T_2$ distribution area of the free/bulk water, both in unit of a.u.; $k_1$ is a conversion coefficient between the NMR signal intensity and the volume of the free/bulk oil: and $k_2$ is a conversion coefficient between the NMR signal intensity and the volume of the free/bulk water; and 2) calibrating an NMR signal intensity and mass of adsorbed oil, particularly comprising steps of:
processing different dry shale samples; fitting relationships between the mass ($m_a-m_0$) and the NMR signal intensity ($T_{2a}-T_{20}$) of the adsorbed oil, wherein: $m_a$ and $T_{2a}$ are respectively mass and NMR $T_2$ distribution signal intensit of the dry shale sample with the adsorbed oil; and, $m_0$ and $T_0$ are respectively mass and NMR $T_2$ distribution signal intensity of the dry shale sample; and obtaining a calibration formula between the MIR signal intensity and the mass of the adsorbed oil that:

$$m_{a0} = k_a \times A_{a0} \quad (3)$$

wherein: in the formula (3), $m_{ao}$ is the mass of the adsorbed oil, in unit of mg; $A_{ao}$ is an NMR $T_2$ distribution area of the adsorbed oil, in unit of a.u.; and $k_a$ is a conversion coefficient between the NMR signal intensity and the mass of the adsorbed oil.

5. The evaluation method for the hydrogen-bearing components, the porosity and the pore size distribution of the organic-rich shale, as recited in claim 2, wherein:
evaluation for the porosity of the organic-rich shale comprises steps of:
acquiring an NMR $T_2$ distribution of saturating oil and calculating the porosity, particularly comprising steps of:
processing the oil-saturated shale sample with an NMR $T_2$ distribution test, and obtaining an NMR $T_2$ decay curve (S(t, sat)) of the oil-saturated shale sample; subtracting an NMR $T_2$ decay curve (S(t, dry)) of the dry shale sample from the NMR $T_2$ decay curve (S(t, sat)) of the oil-saturated shale sample, and obtaining a $T_2$ decay curve ($\Delta S(t, oil)$) of the saturating oil that:

$$S(t, dry) = \sum_i A_i \exp\left(-\frac{t}{T_{2i}}\right); \quad (4)$$

$$S(t, sat) = \sum_j A_j \exp\left(-\frac{t}{T_{2j}}\right); \quad (5)$$

$$\Delta S(t, oil) = S(t, sat) - S(t, dry) \quad (6)$$
$$= \sum_k \Delta A_k \exp\left(-\frac{t}{T_{2k}}\right);$$

wherein: in the formulas (4)-(6), S(t, dry) is an echo amplitude of the dry shale sample; S(t, sat) is an echo amplitude of the oil-saturated shale sample; $\Delta S(t, oil)$ is an echo amplitude of the saturating oil; $A_i$ is an amplitude of the dry shale sample when $T_2=T_{2i}$; $A_j$ is an amplitude of the oil-saturated shale sample when $T_2=T_{2j}$, $\Delta A_k$ is an amplitude of the saturating oil when $T_2=T_{2k}$; t=n* TE, wherein n is number of echoes; i, j and k respectively represent orders of signal collection points, with a value of 1,2,3. . . n; and
the NMR characterization method for the pore size distribution of the organic-rich shale comprises steps of:
determining a calibration coefficient C; according to the formula (1), converting signal intensities corresponding to all $T_2$ points in the NMR $T_2$ distribution of the saturating oil to pore volumes; and, with a specified calibration coefficient C, converting a $T_2$ relaxation time to a pore diameter through a formula of:

$$d = C \times T_2 \quad (7)$$

wherein: in the formula (7), d is the pore diameter, in unit of nm; $T_2$ is an NMR transverse relaxation time, in unit of ms; and C is the calibration coefficient;

with a horizontal axis of pore diameter and a vertical axis of dV/(dlogD), graphing a pore size distribution curve $R_{NMR}$ converted from the NMR $T_2$ distribution of the saturating oil; superimposing a pore size distribution curve $R_{MICP}$ of high-pressure mercury injection with a pore size distribution curve $R_{LTNA}$ of low-temperature nitrogen adsorption; selecting a connection pore diameter $r_p$ at a pore diameter range of 10-100 nm, wherein dV/(dlogD) values of two pore size distribution curves at the point of connection pore diameter $r_p$, are required to be roughly the same, ensuring that the pore number measured by a low-temperature nitrogen adsorption method and a high-pressure mercury injection method is almost identical at the pore diameter $r_p$; remaining data points which are smaller than $r_p$ in the low-temperature nitrogen adsorption method and larger than $r_p$ in the high-pressure mercury injection method, and constructing a full pore size distribution curve $R_{LTNA\text{-}MICP}$ of the shale; superimposing curves of $R_{LTNA\text{-}MICP}$ and $R_{NMR}$, and calculating an error value thereof through a formula of:

$$Q = \frac{1}{n} \sum_{i=1}^{n} \sqrt{(R_{LTNA-MICP-i} - R_{NMR-i})^2} \quad (8)$$
$$= \frac{1}{n} \sum_{i=1}^{n} \sqrt{(R_{LTNA-MICP-i} - C \times T_{2i})^2} \, ;$$

wherein: in the formula (8), Q is the error value; n is a number of data points in the $R_{LTNA\text{-}MICP}$ pore size distribution curve; $R_{LTNA\text{-}MICP}$ is an $i^{th}$ data point in the $R_{LTNA\text{-}MICP}$ pore size distribution curve; and $R_{NMR\text{-}i}$ is $R_{NMR}$ data corresponding to the $i^{th}$ data point in the $R_{LTNA\text{-}MICP}$ pore size distribution curve;

when similarity of the curves of $R_{LTNA\text{-}MICP}$ and $R_{NMR}$ is closest, namely the error value is smallest, recording a current value of the calibration coefficient C as a pore diameter calibration coefficient value of the NMR transverse relaxation time.

\* \* \* \* \*